US012599127B2

(12) United States Patent
Lin et al.

(10) Patent No.:  US 12,599,127 B2
(45) Date of Patent:  Apr. 14, 2026

(54) VITRIFICATION DEVICE AND METHOD FOR PREPARING SAMPLE

(71) Applicant: Nexpring US Opco Inc., Beverly, MA (US)

(72) Inventors: Sabrina C. Lin, Santa Ana, CA (US); Hsiao-Tzu Ni, Santa Ana, CA (US)

(73) Assignee: NEXPRING US OPCO INC., Beverly, MA (US)

( * ) Notice: Subject to any disclaimer, the term of this patent is extended or adjusted under 35 U.S.C. 154(b) by 1249 days.

(21) Appl. No.: 16/606,717

(22) PCT Filed: Apr. 20, 2018

(86) PCT No.: PCT/US2018/028672
§ 371 (c)(1),
(2) Date: Oct. 18, 2019

(87) PCT Pub. No.: WO2018/195496
PCT Pub. Date: Oct. 25, 2018

(65) Prior Publication Data
US 2020/0093122 A1     Mar. 26, 2020

Related U.S. Application Data

(60) Provisional application No. 62/488,655, filed on Apr. 21, 2017.

(51) Int. Cl.
*A01N 1/147*          (2025.01)
*A01N 1/162*          (2025.01)
(Continued)

(52) U.S. Cl.
CPC ............. *A01N 1/147* (2025.01); *A01N 1/162* (2025.01); *B01L 3/0275* (2013.01); *C12M 45/22* (2013.01); *C12N 5/061* (2013.01)

(58) Field of Classification Search
None
See application file for complete search history.

(56) References Cited

U.S. PATENT DOCUMENTS 6,637,463 B1 * 10/2003 Lei ........................... B01L 13/02
137/841
2009/0123992 A1    5/2009 Chin
(Continued)

FOREIGN PATENT DOCUMENTS

CN          101200706 A      6/2008
CN          101272861 A      9/2008
(Continued)

OTHER PUBLICATIONS

Foreign Action other than Search Report on IN 201917047297 DTD May 25, 2021; 6 pages.
(Continued)

*Primary Examiner* — Paul S Hyun
(74) *Attorney, Agent, or Firm* — Gray Ice Higdon

(57)          ABSTRACT

Provided herein are devices and related methods for rapidly freezing a sample using, for example, liquid nitrogen. The device includes an input portion with an input port, a sample chamber, a waste reservoir in fluid communication with the sample chamber, and a filtering mechanism that selectively allows a fluid introduced through the input port to pass through the sample chamber and into the waste reservoir, while retaining a sample within the sample chamber. The sample chamber, waste reservoir, and filtering mechanism are configured to draw fluid from the sample chamber through the filtering mechanism and into the waste reservoir via capillary action.

18 Claims, 23 Drawing Sheets

(51) Int. Cl.
    *B01L 3/02*          (2006.01)
    *C12M 1/00*        (2006.01)
    *C12N 5/076*     (2010.01)

(56)               References Cited

U.S. PATENT DOCUMENTS

| | | | |
|---|---|---|---|
| 2011/0207112 A1 | 8/2011 | Burbank et al. | |
| 2014/0342454 A1 | 11/2014 | Burbank et al. | |
| 2015/0044765 A1* | 2/2015 | Inoue | A01N 1/147 |
| | | | 435/307.1 |
| 2018/0255765 A1* | 9/2018 | Arav | A01N 1/0268 |

FOREIGN PATENT DOCUMENTS

| | | | |
|---|---|---|---|
| CN | 105831105 A | 8/2016 | |
| JP | 2007-520693 A | 7/2007 | |
| JP | 2020-517269 A | 6/2020 | |
| RU | 2349846 | 3/2009 | |
| RU | 164979 U1 | 9/2016 | |
| WO | WO-02/055673 A1 | 7/2002 | |
| WO | WO-2009/105813 A1 | 9/2009 | |
| WO | WO-2013/098825 A1 | 7/2013 | |
| WO | WO-2016/001933 A1 | 1/2016 | |
| WO | WO-2017/064715 | 4/2017 | |

OTHER PUBLICATIONS

Office Action mailed Apr. 8, 2021 in corresponding Chinese application No. 201880039625.5 (7 pages) and English translation 6 pages).

Preliminary Rejection dated Feb. 26, 2023 issued in KR Application No. 10-2019-7033822, with English translation, 5 pages.

Foreign Action other than Search Report on BR 112019022066-6 DTD May 31, 2022.

Foreign Action other than Search Report on JP 2019-557379 DTD Feb. 15, 2022.

Foreign Action other than Search Report on RU 2019136692 DTD Sep. 3, 2021.

Office Action dated Apr. 4, 2023 issued in BR Application No. 112019022066-6 with English translation, 8 pages.

First Office Action dated Nov. 16, 2022 issued in CN Application No. 202210117840.0, with English translation, 15 pages.

Notice of Reasons for Refusal dated Dec. 6, 2022 issued in JP Application No. 2019-557379, with English translation, 6 pages.

International Preliminary Report on Patentability mailed Oct. 31, 2019 in corresponding International Application No. PCT/US2018/028672, 8 pages.

International Search Report and Written Opinion of the International Searching Authority in PCT/US2018/028672 mailed Sep. 8, 2018, 14 pages.

Extended European Search Report dated Oct. 25, 2023 issued in EP Application No. 23174470.7, 15 pages.

Ng, Kelvin, et al., "Paper-based cell culture platform and its emerging biomedical applications," Materials Today, vol. 20, No. 1, Jan./Feb. 2017, pp. 32-44, XP093092220.

Partal European Search Report dated Jul. 17, 2023 issued in EP Application No. 23174470.7, 13 pages.

Liu, Zhi, et al., "Experimental and numerical studies on liquid wicking into filter papers for paper-based diagnostics", Applied Thermal Engineering, vol. 88, Sep. 2015, pp. 280-287, XP093092225.

Technical Examination Report dated Nov. 7, 2023 issued in BR Application No. BR112019022066-6, with English translation, 8 pages.

Foreign Action other than Search Report on JP Appl. Ser. No. 2023-094705 dated Jul. 23, 2024, 10 pages.

Foreign Action other than Search Report on KR Appl. Ser. No. 10-2023-7043090 dated Aug. 30, 2024, 7 pages.

Korean Intellectual Property Office, Notice of Final Rejection issued in Application No. 10-2023-7043090, 6 pages, dated May 22, 2025.

European Patent Office, Examination Report issued in Application No. 23174470.7, 10 pages, dated Mar. 11, 2026.

\* cited by examiner

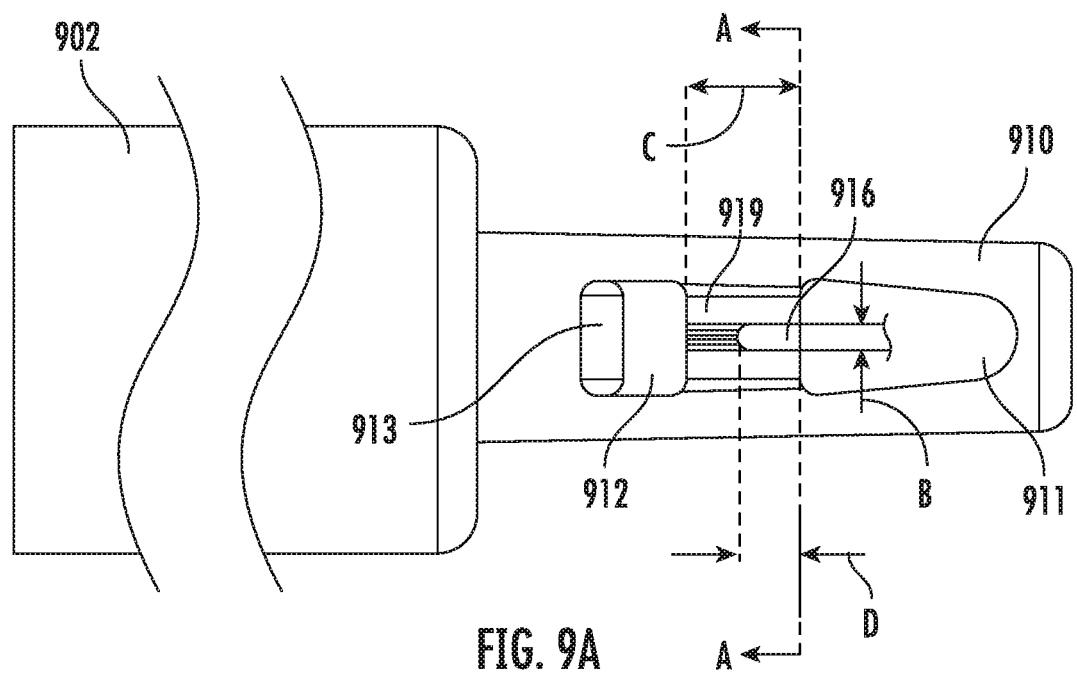
FIG. 9A
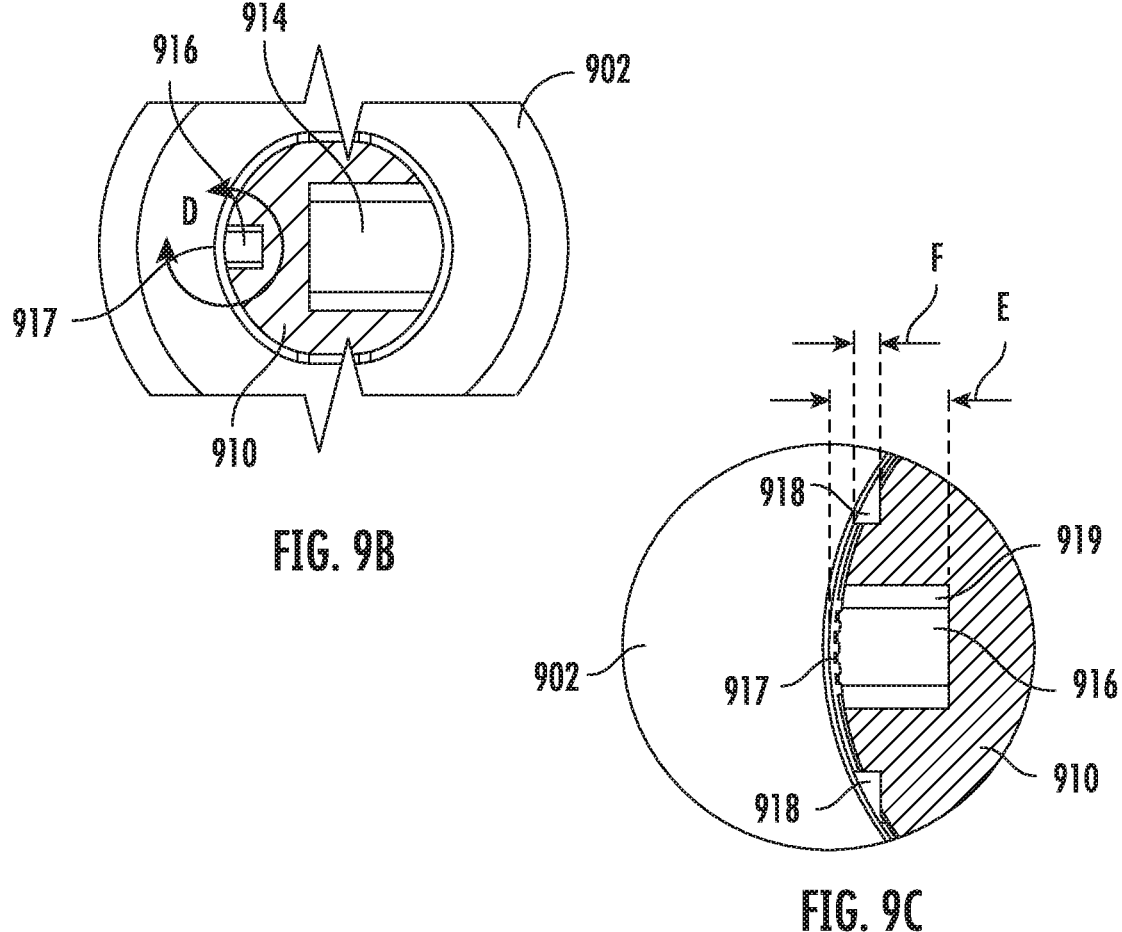
FIG. 9B
FIG. 9C

WASTE RESERVOIR

DEPOSIT EMBRYOS ONTO THE
DEVICE USING MICROPIPETTE

INPUT PORT

QUICKLY PLUNGE
DEVICE INTO LN2

VITRIFICATION DEVICE AND METHOD FOR PREPARING SAMPLE

CROSS-REFERENCE TO RELATED APPLICATIONS

The present application is a U.S. National Stage of International Application No. PCT/US2018/028672 filed on Apr. 20, 2018, which claims the benefit of U.S. Provisional Patent Application No. 62/488,655 filed on Apr. 21, 2017, the entire disclosures of all of which are incorporated herein by reference.

TECHNICAL FIELD

The present disclosure relates generally to vitrification devices and methods for preparing samples.

BACKGROUND

Human oocyte cryopreservation (egg freezing) is one of the techniques used in preserving female fertility. A woman's oocytes are extracted, frozen and stored. In the future, the eggs can be thawed, fertilized, and transferred to the uterus as embryos. Alternatively, a fertilized embryo may be frozen and stored, and later thawed and transferred to the uterus of a woman.

Vitrification is a fast freezing process where a biological specimen is frozen within seconds using, for example, liquid nitrogen. Vitrification of oocytes or embryos has been shown to produce far superior results than those obtained with slow-freezing techniques, in terms of preservation of fertility and viability of oocytes and embryos.

A biological specimen to be preserved by vitrification typically has a small size and is very delicate and susceptible to damage and loss of activity during human manipulation, such as during transfer by micropipetting. Conventionally, samples are pre-treated and prepared for vitrification using various agents or solutions before being transferred to a vitrification tool to be held and exposed to liquid nitrogen. Similarly, for thawing, the frozen sample is also treated with various warm agents or solutions. Each manipulation step involves transferring the specimen, such as an oocyte or embryo, from one solution to another using a micropipetter. Thus the conventional process and tools bear a substantial risk of sample damaging, and human errors and variations associated with such manipulation cannot be avoided.

Thus, there exists a need in this field for new vitrification devices and processes associated therewith for vitrification of biological specimens, with substantially reduced risks for sample damage and human errors.

SUMMARY

An aspect of the present disclosure relates to a vitrification device. In some embodiments, the device comprises an input portion with an input port, a sample chamber, a waste reservoir in fluid communication with the sample chamber, and a filtering mechanism that selectively allows a fluid introduced through the input port to pass through the sample chamber and into the waste reservoir, while retaining a sample within the sample chamber. In some embodiments, the sample chamber, waste reservoir, and filtering mechanism are configured to draw fluid from the sample chamber through the filtering mechanism and into the waste reservoir via capillary action.

In some embodiments, the vitrification device further comprises at least one viewing window, wherein the viewing window is configured such that sample within the sample chamber is viewable through the viewing window.

In some embodiments, the vitrification device further comprises a cap capable of reversibly coupling to the input portion to close the input port. In some embodiments, the cap is configured to seal the input port so as to inhibit flow of fluid within the vitrification device when the cap is coupled to the input portion. In some embodiments, the filtering mechanism comprises a filter having a plurality of pores sized and configured to form a plurality of microfluidic channels for promoting capillary action.

In some embodiments, the sample chamber comprises a material resistant to liquid nitrogen. In some embodiments, the sample chamber comprises a thermal conducting material. In some embodiments, the sample chamber is formed of at least one of: an acrylic-based material, a polypropylene-based material, a polycarbonate-based material and a copolyester-based material. In some embodiments, the sample chamber has a wall with a thickness less than or equal to 0.002 inches.

Another aspect of the present disclosure relates to a method for preparing a sample. In some embodiments, the method comprises delivering a sample into a sample chamber and adjacent a filtering mechanism, and treating the sample with a first fluid by pushing the first fluid through the sample chamber and into a waste reservoir with a fluidic force, while the filtering mechanism retains the sample within the sample chamber. Pushing the first fluid into the waste reservoir initiates capillary action, to draw subsequent fluids through the sample chamber and into the waste reservoir In some embodiments, the method further comprises treating the sample with a second fluid by drawing the second fluid through the sample chamber and into the waste reservoir via capillary action, while the filtering mechanism retains the sample within the sample chamber. In some embodiments, the method further comprises viewing the sample in the sample chamber through a viewing window in the sample chamber.

In some embodiments, the method further comprises sealing an input port for flowing fluid into the sample chamber by coupling a cap. In some embodiments, the method further comprises vitrifying the sample in the sample chamber. In some embodiments, the sample is vitrified by contacting the sample chamber with liquid nitrogen.

In some embodiments, the method further comprises thawing the sample by contacting the sample chamber with a warm solution.

BRIEF DESCRIPTION OF THE DRAWINGS

FIG. 9A is a top view of a portion of a vitrification device according to some embodiments of the present disclosure.

FIG. 9B is a cross-sectional view of the vitrification device taken the along line A-A of FIG. 9A.

FIG. 9C is an enlarged view of area D as shown in FIG. 9B according to some embodiments of the present disclosure.

DETAILED DESCRIPTION

Provided herein are devices and methods for rapidly freezing a sample using, for example, liquid nitrogen. In certain preferred embodiments, low pressure forces, such as those generated by capillary action, can be used to push or draw fluid through the device without damaging sample(s) in the device.

Figure 1:
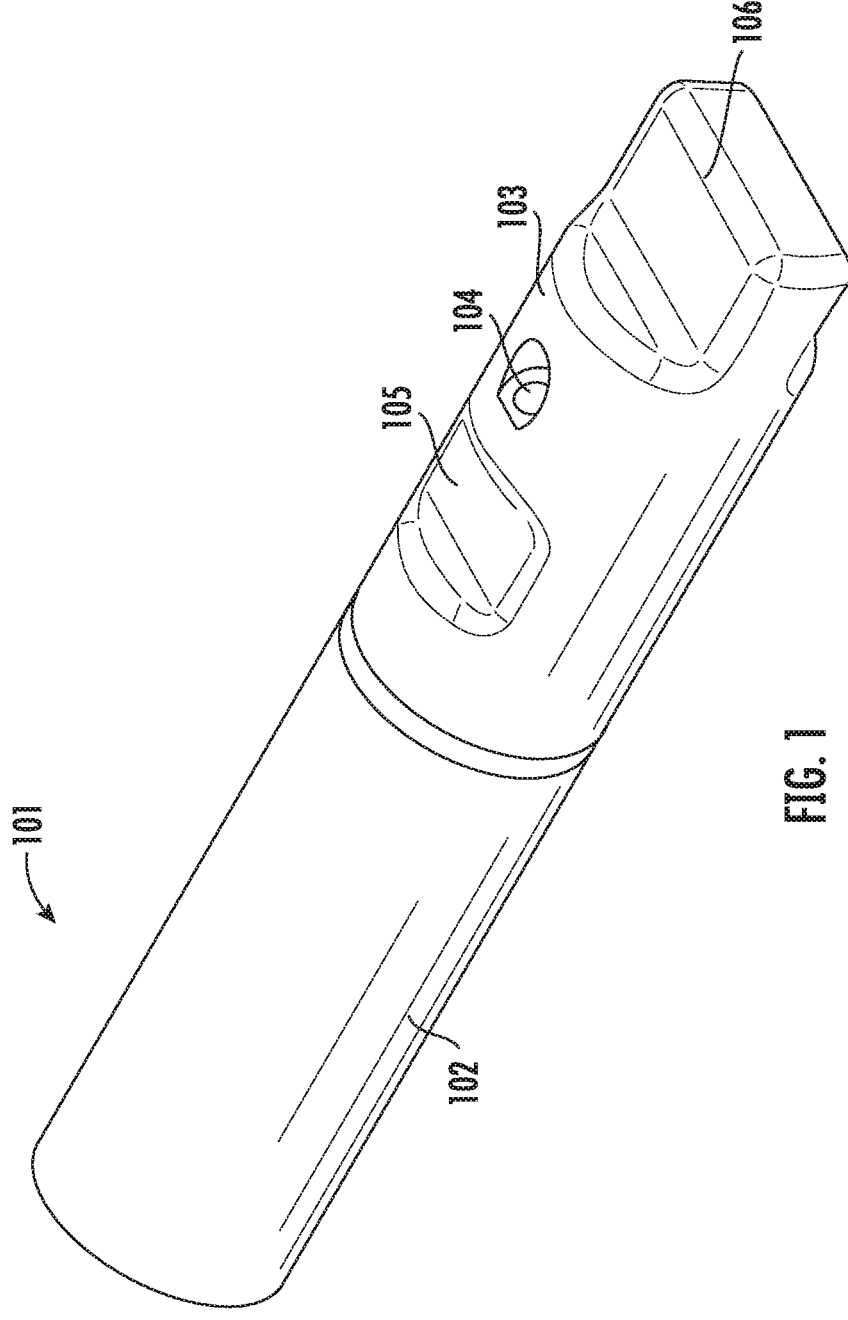
FIG. 1 is a perspective view of a portion of a vitrification device according to some embodiments of the present disclosure.

Referring to FIG. 1, a perspective view of the vitrification device 101 according to one embodiment of the present disclosure is shown. The vitrification device 101 comprises an elongated shape and two ends. On one end, the device 101 comprises an input portion (not shown) reversibly coupled to a removable cap 103. On the other end, the device 101 comprises a handle 102. The cap 103 is coupled to the input portion, and is able to rotate around the longitudinal axis of the cap 103. The vitrification device 101 has a closed configuration and at least one open configuration. In some embodiments, switching between the closed and open configurations is achieved by rotating the cap 103. In some embodiments, the coupling between the cap 103 and the input portion may be reversible, and the cap 103 can be removed from the input portion if a user desires.

Figures 2A, 2B, 2C:
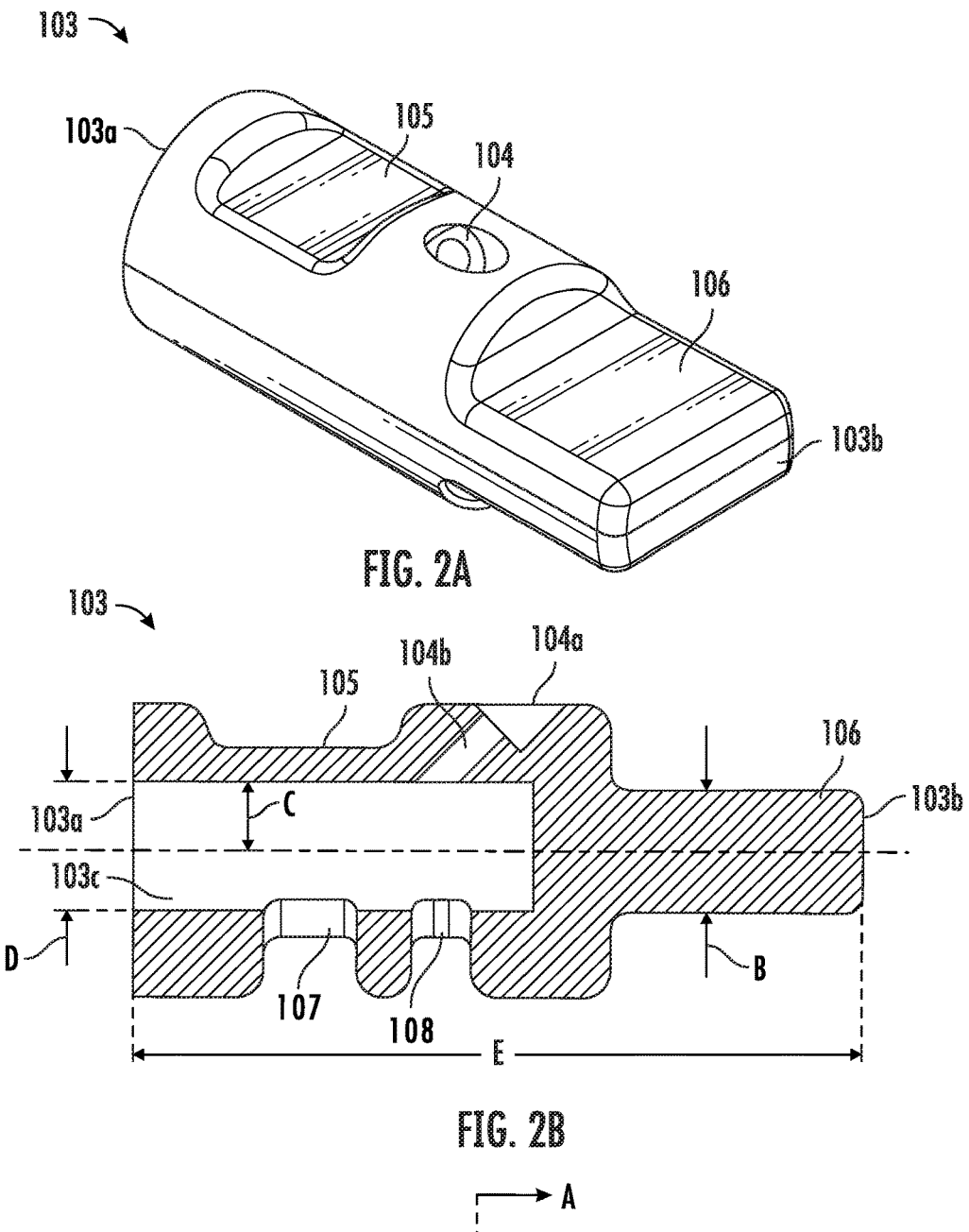
FIG. 2A is a perspective view of a cap of the vitrification device according to some embodiments of the present disclosure.
FIG. 2B a cross-sectional view of the cap of FIG. 2A according to some embodiments of the present disclosure.
FIG. 2C is a front view of the cap of FIG. 2A according to some embodiments of the present disclosure.

FIG. 2A shows a perspective illustration of the cap 103. The cap 103 has an open end 103a and a closed end 103b. In some embodiments, the cap 103 comprises at least one input port 104 and at least one viewing window 105. In some embodiments, the cap 103 further comprises one or more openings (not shown). In some embodiments, the closed end 103b forms a grip 106 for easy holding and rotating of the cap 103.

FIG. 2B shows the cap 103 according one example embodiment of the present disclosure. The cap 103 assumes roughly the shape of a hollow cylinder with several recesses and/or openings on the side of the cylinder. The cap 103 has an open end 103a and a closed end 103b. FIG. 2B shows the cross section of the cap 103 along line A-A of the FIG. 2C, which is a front view of the cap 103 taken from the closed end 103b. As shown in this view, the cap 103 has an open end 103*a*, a closed end 103*b* and a hollow space 103*c*. There is at least one input port 104 that connects the hollow space 103*c* with the outside of the cap 103. In this example embodiment, the input port 104 comprises a recess 104*a* on the wall of the cap 103, and an input channel 104*b* that assumes an acute angle with the longitudinal axis of the cap 103, such that a fluidic agent, such as a solution, delivered through the input port 104 flows directly to a sample area located within the hollow space 103*c*. In some embodiments, the angle between the input channel 104*b* and the longitudinal axis of the cap 103 is in the range of about 20° to about 70°. In some embodiments, the angle is 20°, 30°, 40°, 50°, 60°, or 70°.

In some embodiments, the cap 103 also comprises at least one viewing window 105 on the wall. In some embodiments, the viewing window 105 is made of a transparent material, such that a user of the device can easily see through to examine the conditions of a sample located within the hollow space 103*c*. In various embodiments, the viewing window 105 can be made of the same or a different material comparing to the remaining parts of the cap 103. In some embodiments, the viewing window 105 may form a recess on the wall, such that the thickness at the viewing window 105 area is smaller than the average thickness of the wall.

In some embodiments, the cap 103 further comprises one or more openings. In the example embodiment as shown in FIG. 2B, the cap 103 has two openings 107, 108 connecting the hollow space 103*c* with the outside. In some embodiments, when the cap 103 is in contact with liquid nitrogen, liquid nitrogen flows through the openings into the hollow space 103*c* and gets into proximity of a sample located therein. In some embodiments, the number of such openings on the cap 103 is not limited to two. In various embodiments, the cap 103 can have one, two or more than two openings. It is contemplated that in some embodiments, having multiple openings on the cap 103 allows fast flowing of liquid nitrogen to the proximity of the sample area and thus fast vitrification of the sample, as air trapped in the hollow space 103*c* can escape through one opening while liquid nitrogen enters through another.

In the example embodiment shown in FIG. 2B, the thickness of the grip 106, as measured by the distance between arrow pair B, ranges from about 0.06 inch to about 0.12 inch. In one example embodiment, the thickness of the grip 106 is 0.114 inch.

In some embodiments, the diameter of the hollow space 103*c*, as measured by the distance between arrow pair D, ranges from about 0.06 inch to about 0.13 inch. In one example embodiment, the diameter is 0.126 inch. In some embodiments, the hollow space 103*c* is configured to house a tapered input portion of the vitrification device. For example, in some embodiments, the input portion has about 1° draft and the cap 103 has a matching draft of 1° on the internal hollow space 103*c*. When the cap 103 is coupled to the input portion, the tapered shapes create a wedging force that helps to engage and/or seal the two parts. In various embodiments, the input portion and the cap 103 may have a matching draft in the range of 1° to 5°.

In some embodiments, the length of the cap 103, as measured by the distance E, ranges from about 0.3 inch to about 0.7 inch. In one example embodiment, the length of the cap 103 is 0.64 inch.

Figure 3:
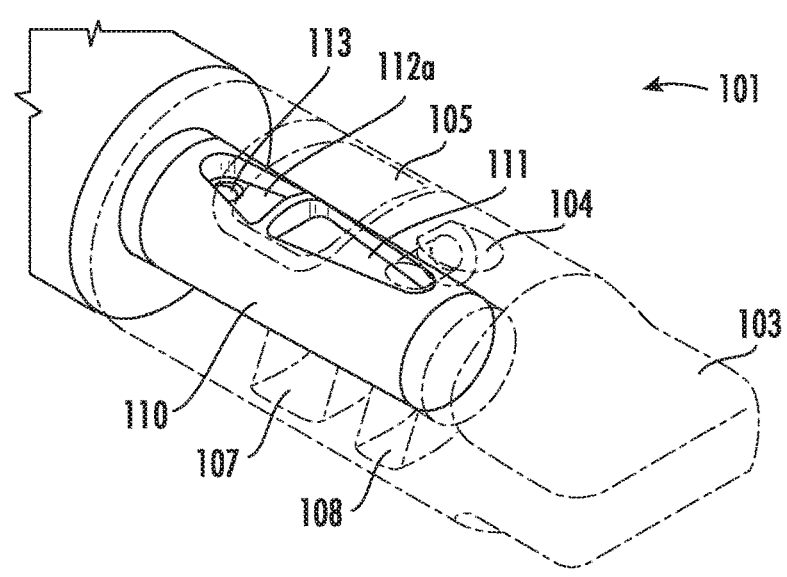
FIG. 3 is a perspective view of an input portion of the vitrification device covered with the cap according to some embodiments of the present disclosure.

FIG. 3 shows a perspective view of the front portion of the vitrification device 101, showing the coupling between the cap 103 and the input portion 110 of the device. Particularly, shown in this view is a first open configuration of the vitrification device 101. In this configuration, the cap 103 is positioned relative to the input portion 110 such that the input port 104 is in fluidic communication with the sample chamber 111, and the viewing window 105 lays over the sample chamber 111. In some embodiments, the input portion 110 further comprises a waste reservoir 112*a* and waste channel 113 for retaining and disposing waste.

Using the first open configuration, a user may deliver a fluidic agent, such as a sample or solutions for preparing or treating the sample, into the sample chamber 111 through the input port 104, while monitoring contents and/or activities within the sample chamber 111 through the viewing window 105. The waste reservoir 112*a* is in fluid communication with the sample chamber 111. Waste is then collected into the waste reservoir 112*a* and disposed through the waste channel 113. In various embodiments, the sample chamber 111 may comprise different mechanisms for retaining the sample while letting through waste to reach the waste reservoir 112.

Figure 4A:
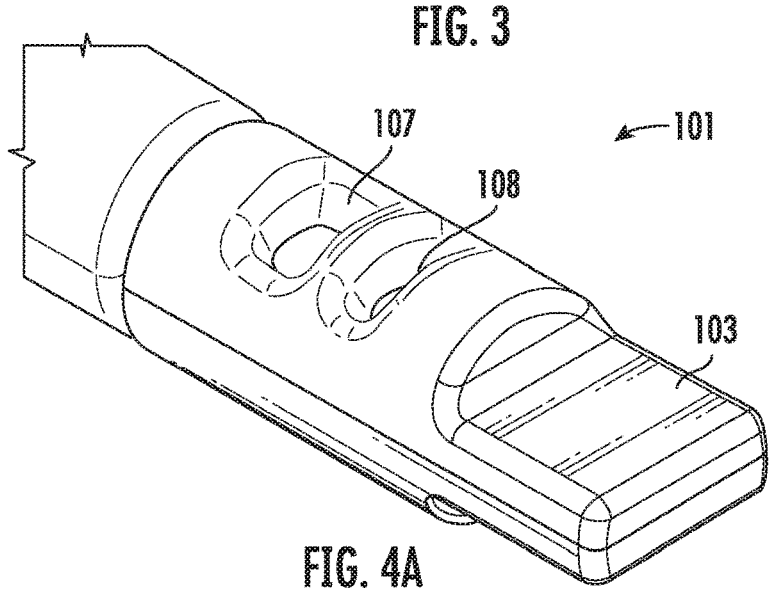
FIG. 4A is a perspective view of a front portion of the vitrification device according to some embodiments of the present disclosure.
Figure 4B:
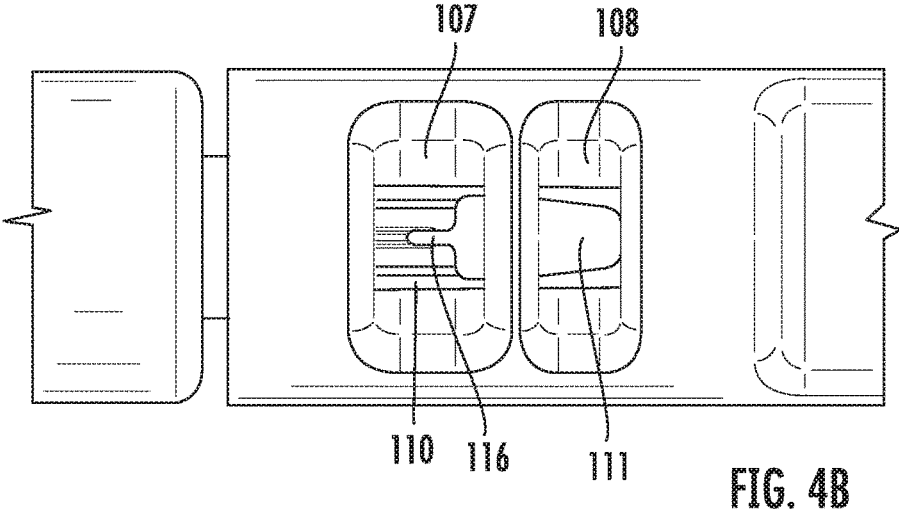
FIG. 4B is a top view of a front portion of the vitrification device according to some embodiments of the present disclosure.

FIGS. 4A and 4B show a perspective view and a top view, respectively, of the vitrification device 101 in a second open configuration. In this configuration, the cap 103 is positioned relative to the input portion 110 such that one or more of the openings 107, 108 on the cap 103 lay over the sample chamber 111. Thus, using this configuration, a user may manipulate and/or retrieve a sample from the sample chamber 111 through at least one of the openings 107, 108. In various embodiments, dimensions of the openings 107, 108 on the cap 103 may be the same or different. Without being bound by theory, it is contemplated that at least one opening 107 is large enough to allow easy manipulation and retrieval of samples through it. Optionally, the other opening(s) 108 may be smaller, as long as the flow of liquid nitrogen through the opening(s) is not hindered by the size.

Figures 5A, 5B, 5C:
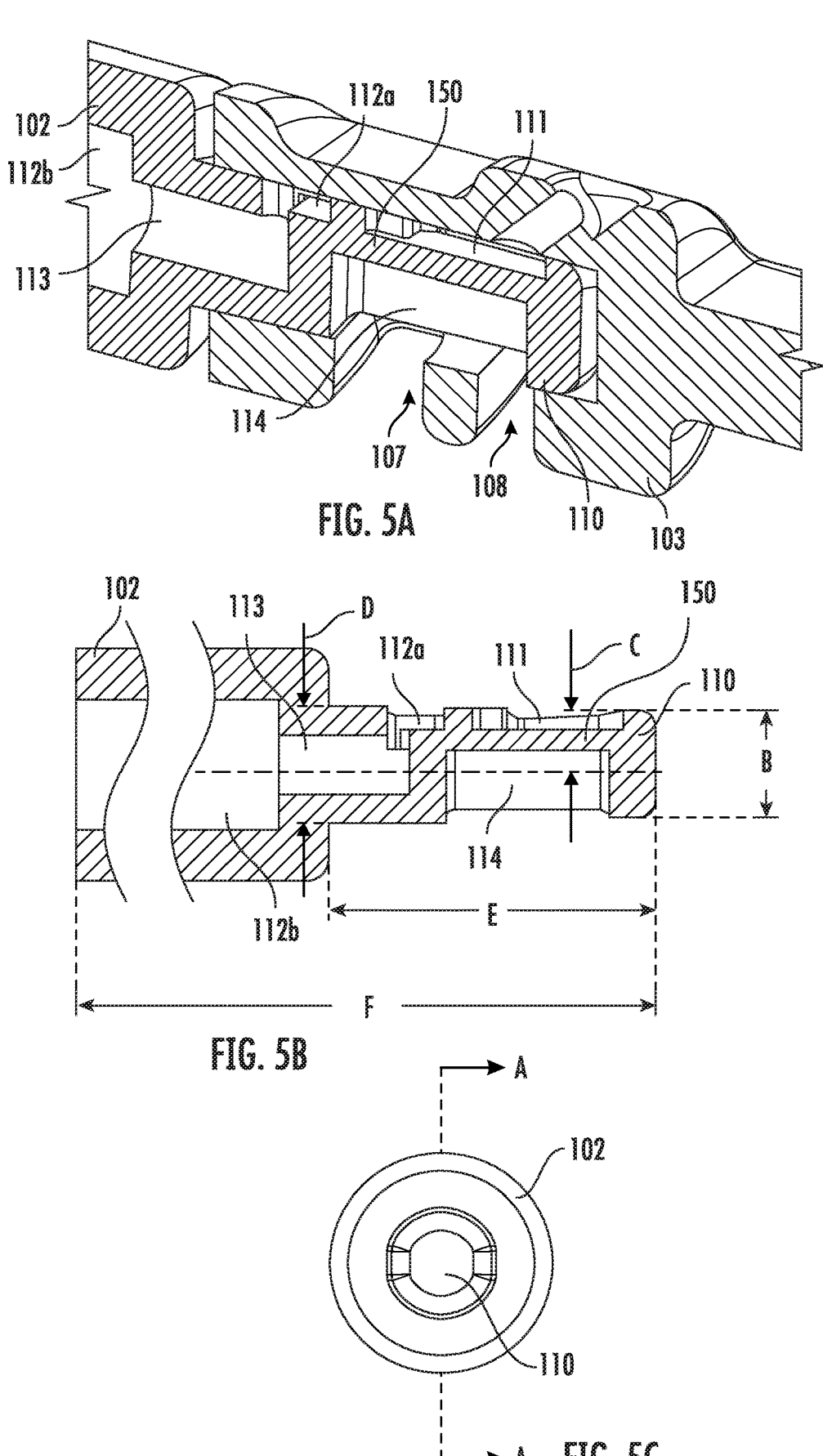
FIG. 5A is a longitudinal cross-sectional view of a portion of the vitrification device according to some embodiments of the present disclosure with the cap is coupled with an input portion of the device.
FIG. 5B is a cross-sectional view of the input portion of the vitrification device according to some embodiments of the present disclosure.
FIG. 5C is a front view of the cap portion of FIG. 5B according to some embodiments of the present disclosure.

FIG. 5A shows a cross-sectional view of the vitrification device 101 as shown in the first open configuration of FIG. 3. As shown in the cross-section view in FIG. 5A, the input portion 110 comprises a sample chamber 111 in fluidic communication with a waste reservoir 112*a*/112*b*. In some embodiments, the waste reservoir 112*b* extends into the handle 102 of the device. As shown in FIG. 5A, the sample chamber 111 is located on the input portion 110, and an input portion waste reservoir 112*a* connects to a waste reservoir 112*b* located inside the handle 102 through a waste channel 113. In some embodiments, the device disposes a fluidic waste into the waste reservoir 112*b* in the handle 102. In some embodiments, the device further comprises a mechanism, such as a check valve, that prevents the waste from moving from the waste reservoir 112*a*/112*b* back into the sample chamber 111. In some embodiments, the device further comprises a mechanism, such as a filter, in the handle 102 that allows trapped air to vent as fluids enter the waste reservoir 112*b*, and prevents liquid nitrogen from entering the waste reservoir 112*b*.

In some embodiments, the input portion 110 further comprises at least one recess 114 in close proximity to the sample chamber 111. Particularly, in the example embodiment as shown in FIG. 5A, the recess 114 is separated from the sample chamber 111 by a thin wall 150. In some embodiments, the cap 103 further comprises at least one opening 107, 108. When the cap is coupled to the input portion in the closed configuration, the openings 107, 108 are in fluidic communication with the recess 114, such that liquid nitrogen may flow into the recess through the openings. In some embodiments, the device is configured for dipping into liquid nitrogen in its closed configuration. Thus, the openings on the cap allow liquid nitrogen to flow into the recess 114 of the input portion 110, thereby getting into close proximity to the sample chamber 111 for faster vitrification of samples contained therein. In some embodiments, the cap 103 comprises at least two openings 107, 108, which allow liquid nitrogen to flow into the recess 114 more easily, as air trapped in the recess can escape through one opening while liquid nitrogen enters through another.

In some embodiments, the dimension of the input portion 110 at different positions along its longitudinal axis may be the same or different. Particularly, in some embodiments, the input portion 110 is tapered. In some embodiments, the internal space of the cap 103 is also tapered to match the shape of the input portion 110. The tapered shapes create a wedging force that helps to engage and seal the input portion 110 with the cap 103. In some embodiments, the input portion 110 and the cap 103 have a matching draft in the range of 1° to 5°.

FIG. 5B shows the cross section of the input portion 110 along line A-A of the FIG. 5C, which is a front view of the input portion 110. As shown, in this example embodiment, the dimension of the input portion 110 gradually gets smaller from where it connects with the handle 102 (the base of the input portion 110) towards the other end of the input portion 110 (the front end of the input portion 110). Particularly, the dimension at the base, as measured in the distance between arrow pair D, is in the range of about 0.1 inch to about 0.2 inch. In one example embodiment, the dimension at the base of the input portion 110 is 0.127 inch. The dimension at the front end of the input portion 110, as measured in the distance between arrow pair B is in the range of about 0.1 inch to about 0.2 inch. In one example embodiment, the dimension at the front end is about 0.116 inch.

In some embodiments, the length of the input portion 110 as measured in the distance between arrow pair E is in the range of about 0.1 inch to about 0.4 inch. In one example embodiment, the length of the input portion 110 is about 0.351 inch. In some embodiments, the length of the device including the handle 102 and input portion 110 as measured by the distance F in FIG. 5B is in the range of about 0.5 inch to about 3 inches.

Figure 6A:
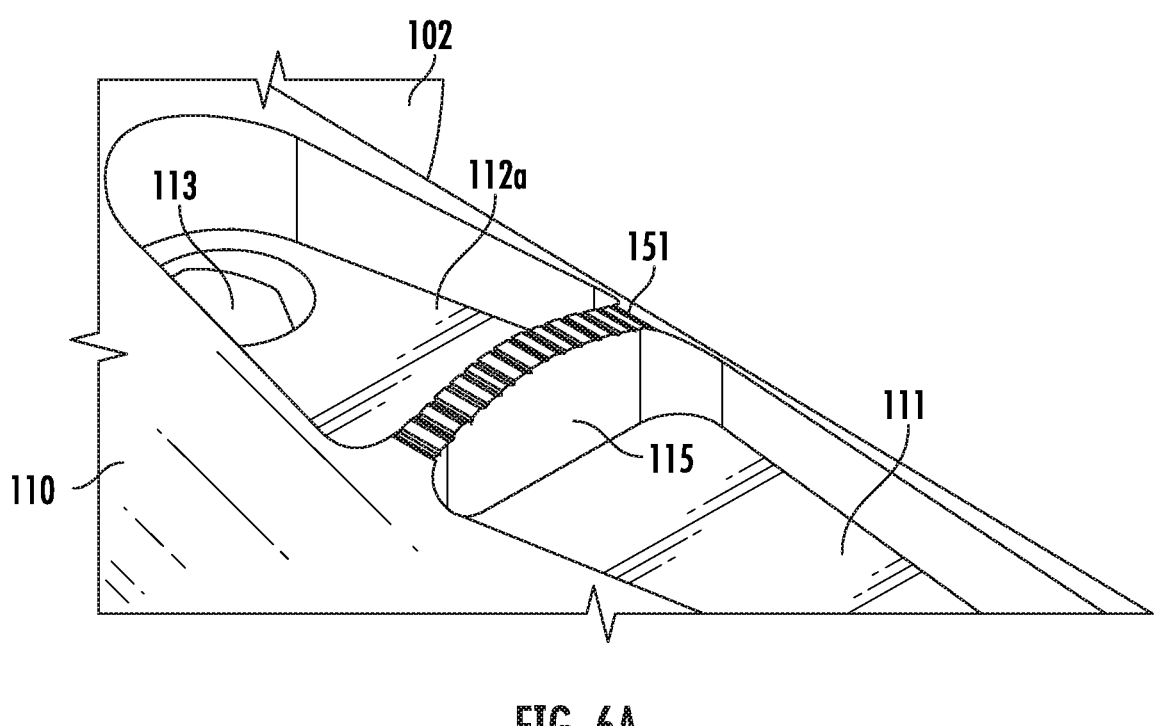
FIG. 6A is a perspective view of a portion of the input portion of the vitrification device according to some embodiments of the present disclosure.
Figure 6B:
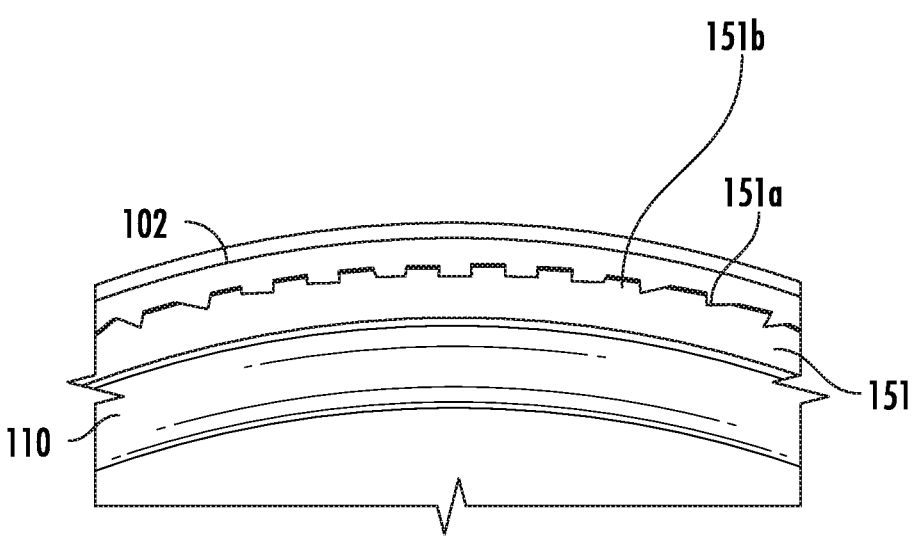
FIG. 6B is a side view of a portion of the filtration grate according to some embodiments of the present disclosure.

FIGS. 6A and 6B illustrate one example embodiment of an input portion of the vitrification device. Particularly, FIG. 6A shows a perspective view of a partial structure of the input portion 110. Shown in this view are part of the handle 102, the waste reservoir 112a and the opening of the waste channel 113, which are located on the input portion 110. Also located on the input portion 110 are the sample chamber 111 and a block 115 which separates the sample chamber 111 and the waste reservoir 112a. In some embodiments, when the cap (not shown) is coupled to the input portion 110, the top of the block 115 engages with the inner wall of the cap. In some embodiments, such as shown in FIG. 6A, the top of the block 115 comprises a filtering mechanism, such as filtration grates 151, that keeps the sample chamber 111 in fluidic communication with the waste reservoir 112 when the cap (not shown) is coupled to the input portion 110.

FIG. 6B is an enlarged view showing partial structures of the filtration grates 151 as shown in FIG. 6A. Also shown are partial structures of the handle 102 and the input portion 110 of the device. In this embodiment, the filtration grates 151 comprise a plurality of alternating lower 151a and taller segments 151b. Thus, when the input portion 110 engages with the cap (not shown), the top of the taller segments 151b engages with the inner wall of the cap, forming channels at the lower segments 151a that connect the waste reservoir 112a and the sample chamber 111 in fluidic communication.

In some embodiments, when the cap is on, a fluid-delivering device, such as a micropipette, can be used to push a waste fluid through the channels into the waste reservoir, while a sample such as an oocyte or embryo is retained in the sample area. Thus, in some embodiments, the dimension of the filtration grates 151 depends on the type of sample to be used with the vitrification device. In some embodiments, the dimension is selected such that the channels let through the waste but retain a sample. For example, in the embodiments where the sample is human oocyte or embryo, a dimension (such as a diameter, a width or length depending on the shape of the channel) of each channel is in the range from 0.0005 to 0.0015 inch.

Further, not intended to be bound by theory, it is contemplated that the dimension of the channels also affects the liquid pressure on the sample located in the sample chamber. The number of channels is not critical, and the device works with one or more than one channels. In some embodiments, it is contemplated that the multiple-channel design assists in decreasing a back pressure which allows quick fluid filling and less stress on the sample in the sample area.

In some embodiments, the filtration grates 151 form a single channel connecting the sample chamber and the waste reservoir, and the flow area (defined as the cross-sectional area perpendicular to the longitudinal axis of the channel) is in the range of about $7 \times 10^{-7}$ in$^2$ to $1.5 \times 10^{-6}$ in$^2$. In other embodiments, the filtration grates 151 form multiple channels connecting the sample chamber and the waste reservoir, and the total flow area of all channels combined is in the range of about $7 \times 10^{-7}$ in$^2$ to $1.5 \times 10^{-6}$ in$^2$.

As can be now appreciated, in some embodiments, the filtration grates 151 facilitate separation of a fluidic waste from a particular sample contained in the sample chamber 111. In some embodiments, the filtration grates 151 facilitate removal of the waste out of the sample chamber. Particularly, in some embodiments, the fluidic waste flows into the waste reservoir 112a through the channels formed by the filtration grates 151, while samples having particle sizes greater than the diameter of the channels are retained in the sample chamber 111. The flow of the fluids within the present device can be driven by various mechanisms. For example, in some embodiments, when the cap engages with the input portion, a fluid-delivering device, such as a micropipette, can deliver a fluidic pressure into the sample chamber through the input port, and push the fluidic flow towards the waste reservoir. In alternative embodiments, a suction mechanism may draw the flow of fluids towards the waste reservoir. Further, in some embodiments, the micro-fluidic channels formed by the filtration gates 151 are configured to provide a capillary wicking power that facilitates drawing the liquid waste towards the waste reservoir. The capillary action is initiated when a first solution is introduced through the input port 104 with a fluidic force, such as by using a pipet. The fluid is pushed through the sample chamber 111, through the filtration gates 151, and into the waste reservoir 112. The presence of fluid in the waste reservoir 112, in combination with the particularly sized microfluidic channels throughout the entirety of the device, generates a force strong enough to pull subsequent fluids through the device 101 using capillary action.

Figures 7A, 7B, 7C:
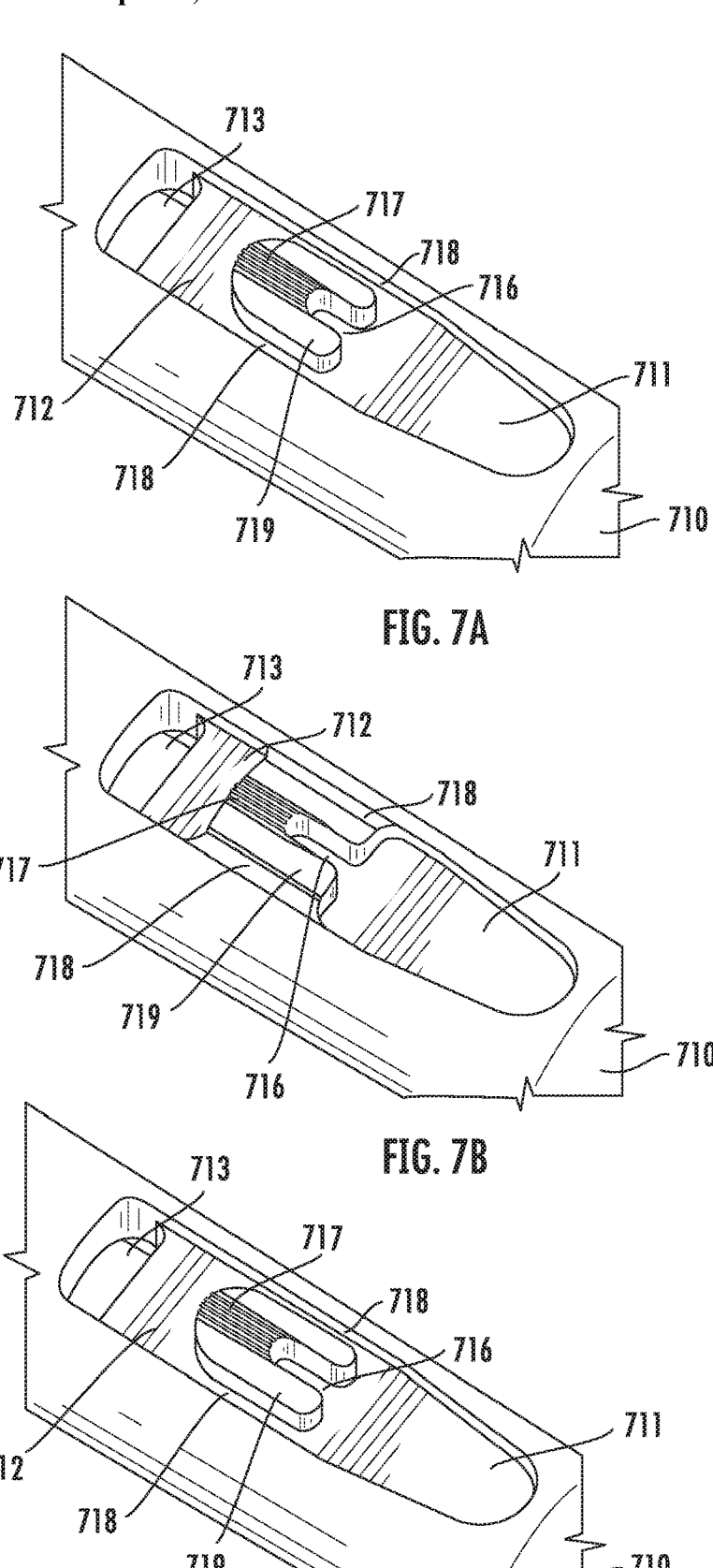
FIGS. 7A-7C are partial views of various embodiments of an input portion of a vitrification device according to some embodiments of the present disclosure.

FIGS. 7A-7C illustrate additional example embodiments of the vitrification device. Particularly, FIG. 7A is a perspective view of a partial structure of the input portion 710. In this embodiment, an island 719 separates the sample chamber 711 and the waste reservoir 712. Bypass channels 718 on both sides of the island 719 connect the sample chamber 711 and the waste reservoir 712 in fluidic communication. In some embodiments, the island 719 further comprises a capture pocket 716 configured to capture and retain a sample therein. The capture pocket 716 has an open end towards the sample chamber 711, and a closed end towards the waste reservoir 712. As shown in the figure, in some embodiments, the capture pocket 716 assumes a "U" shape.

In some embodiments, the top of the island 719 further comprises a filtering mechanism, such as a plurality of filtration channels 717, which connects on one end with the capture pocket 716, and on the other end with the waste reservoir 712. When the cap (not shown) is coupled with the input portion 710, the top surface of the island 719 engages with the inner wall of the cap, and the filtration channels 717 connect the capture pocket 716 with the waste reservoir 712 in fluidic communication.

According to the present disclosure, the dimension of the filtration channels and bypass channels may vary. FIG. 7B illustrates an example embodiment, in which the bypass channels 718 are partially filled along the bottom, thereby restricting the channels 718 to a smaller dimension. Not intended to be bound by theory, it is contemplated that the dimensions of the bypass channels 718 and the filtration channels 717 affect the amount of fluidic flow over the sample located in the capture pocket 716, as well as the liquid pressure on the sample. It is not critical to define the number of bypass channels 718 or filtration channels 717. The present device can work with at least one bypass channel 718 and at least one filtration channel 717. As used herein, the flow area of a channel is defined as the area of the cross section perpendicular to the longitudinal axis of the channel. In some embodiments, the total flow area of the bypass channel(s) is in the range of about $5\times10^{-6}$ in$^2$ to $2\times10^{-5}$ in$^2$. In some embodiments, the total flow area of the filtration channel(s) is in the range of about $7\times10^{-7}$ in$^2$ to $1.5\times10^{-6}$ in$^2$.

In some embodiments, a ratio between the total flow area of the bypass channels and the total flow area of the filtration channels is selected to achieve optimal flow and fluidic pressure over the sample in the capture pocket. It is contemplated that a higher bypass to filtration ratio drives more fluids to flow through the bypass channels (i.e., bypassing the capture pocket), and thus the sample in the capture pocket receives less fluidic treatment. A lower ratio drives more fluids to flow through the capture pocket and the filtration channels, thereby creating a higher liquid pressure on the sample. Accordingly, in some embodiments, the bypass to filtration ratio is in the range of about 6:1 to about 4:1. Particularly, in some embodiments, the bypass to filtration ratio is about 5:1.

In some embodiments, the dimension of the filtration channel is also selected based on the type of sample to be used with the vitrification device. Particularly, in some embodiments, the dimension of the filtration channel is selected such that it lets through the waste but retains a sample within the capture pocket. For example, in the embodiments where the sample is human oocyte or embryo, the diameter of each filtration channel is in the range from 0.0005 to 0.0015 inch.

Figure 8A:
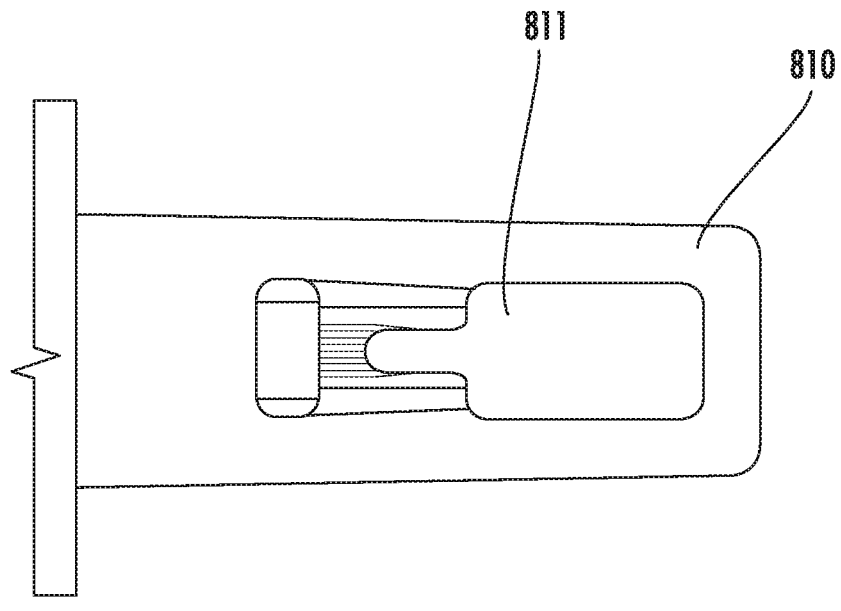
FIGS. 8A-8B are top views of various embodiments of an input portion of a vitrification device according to some embodiments of the present disclosure.
Figure 8B:
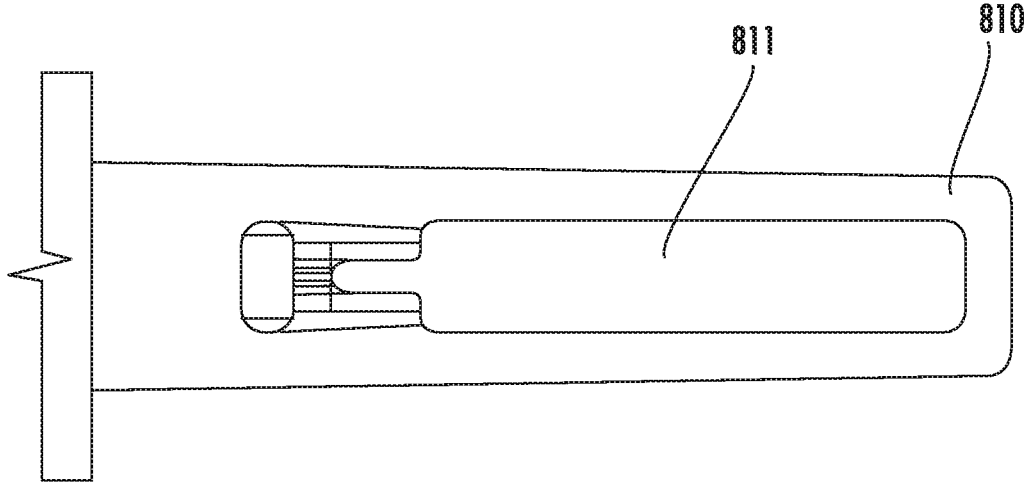

According to the present disclosure, the size of the capture pocket may vary. For example, FIG. 7C illustrates an example embodiment, in which the length of the capture pocket 916 is increased as compared to the embodiment as shown in FIG. 7A. In other embodiments, the thickness and/or width of the capture pocket 716 may vary. In some embodiments, the volume of the capture pocket is sufficient to hold a few oocytes or embryos of human or animal. In some embodiments, the size of the sample chamber 711 on the input portion 910 may vary. For example, FIGS. 8A and 8B illustrate two example embodiments, where in FIG. 8A, the length of the input portion 810 housing the sample chamber 811 is elongated as compared to FIG. 8B.

FIGS. 9A-9C are schematic illustrations of one embodiment of the vitrification device according to the present disclosure. FIG. 9A shows the handle 902, the input portion 910, and various structures located on the input portion 910, which include the sample chamber 911, waste reservoir 912, the opening of the waste channel 913, and the island 919. In this embodiment, the island 919 has a U-shaped capture pocket 916 and filtering mechanism, such as a plurality of filtration channels 917, connecting the U-shaped capture pocket 916 with the waste reservoir 912. FIG. 9B shows a cross-sectional view along line A-A of FIG. 9A. Shown in the cross-sectional view are the handle 902, the input portion 910 and various structures located on the input portion 910, which include a recess 914, the capture pocket 916, and a plurality of filtration channels 917. FIG. 9C is an enlarged view of area D as shown in FIG. 9B. Visible from this view include additionally the bypass channels 918.

In some embodiments, the length of the U-shaped capture pocket 916 as measured by the distance between arrow pair D of FIG. 9A ranges from about 0.02 inch to about 0.04 inch; In one example embodiment, the length of the capture pocket 916 is 0.038 inch.

In some embodiments, the width of the capture pocket 916 as measured by the distance between the arrow pair B of FIG. 9A ranges from about 0.005 inch to about 0.02 inch. In one example embodiment, the width of the capture pocket 916 is 0.015 inch.

In some embodiments, the length of the island 919, as measured by the distance between the arrow pair C of FIG. 9A, ranges from about 0.03 inch to about 0.07 inch. In one example embodiment, the length of the island 919 is 0.68 inch.

In some embodiments, the depth of the capture pocket 916 as measured by the distance between the arrow pair E of FIG. 9C ranges from about 0.01 inch to about 0.03 inch. In one example embodiment, the depth of the capture pocket 916 is 0.021 inch.

In some embodiments, the depth of the bypassing channel 918, as measured by the distance between arrow pair F of FIG. 9C ranges from about 0.001 inch to about 0.005 inch. In one example embodiment, the depth of the bypass channel 918 is 0.005 inch.

In some embodiments, when the vitrification device is in the first open configuration, the input port of the cap is placed relative to the input portion such that at least one end of the input port is in close proximity with the capture pocket. Thus, a user can easily deliver a sample into the capture pocket through the input port, using a micropipette for example.

In some embodiments, the filtration channels 717, 917 facilitate separation of a fluidic waste from a particular sample contained in the capture pocket 716, 916. Particularly, in some embodiments, the fluidic waste flows into the waste reservoir 712, 912 through the filtration channels 717, 917, while samples having particle sizes greater than the diameter of the channels are retained in the capture pocket 716, 916. The flow of the fluidic waste can be driven by various mechanisms. For example, in some embodiments, when the cap engages with the input portion, a fluid-delivering device, such as a micropipette, can deliver a fluidic pressure into the sample chamber through the input port, and push the flow of fluids towards the waste reservoir.

In alternative embodiments, a suction mechanism may draw the flow of the fluids towards the waste reservoir. Further, in some embodiments, the microfluidic channels are configured to provide a capillary wicking power that facilitates drawing the liquid waste towards the waste reservoir. The capillary action is initiated when a first solution is introduced to the sample chamber 711, 911 with a fluidic force, such as by using a pipet. The fluid is pushed through the sample chamber 711, 911, through the filtration channels 717, 917 and into the waste reservoir 712, 912 and waste channel 713, 913. The presence of fluid in the waste channel 713, 913, in combination with the particularly sized microfluidic channels through the entirety of the device, generates a force strong enough to pull subsequent fluids through the device 701, 901 using capillary action.

Figures 10A, 10B, 10C:
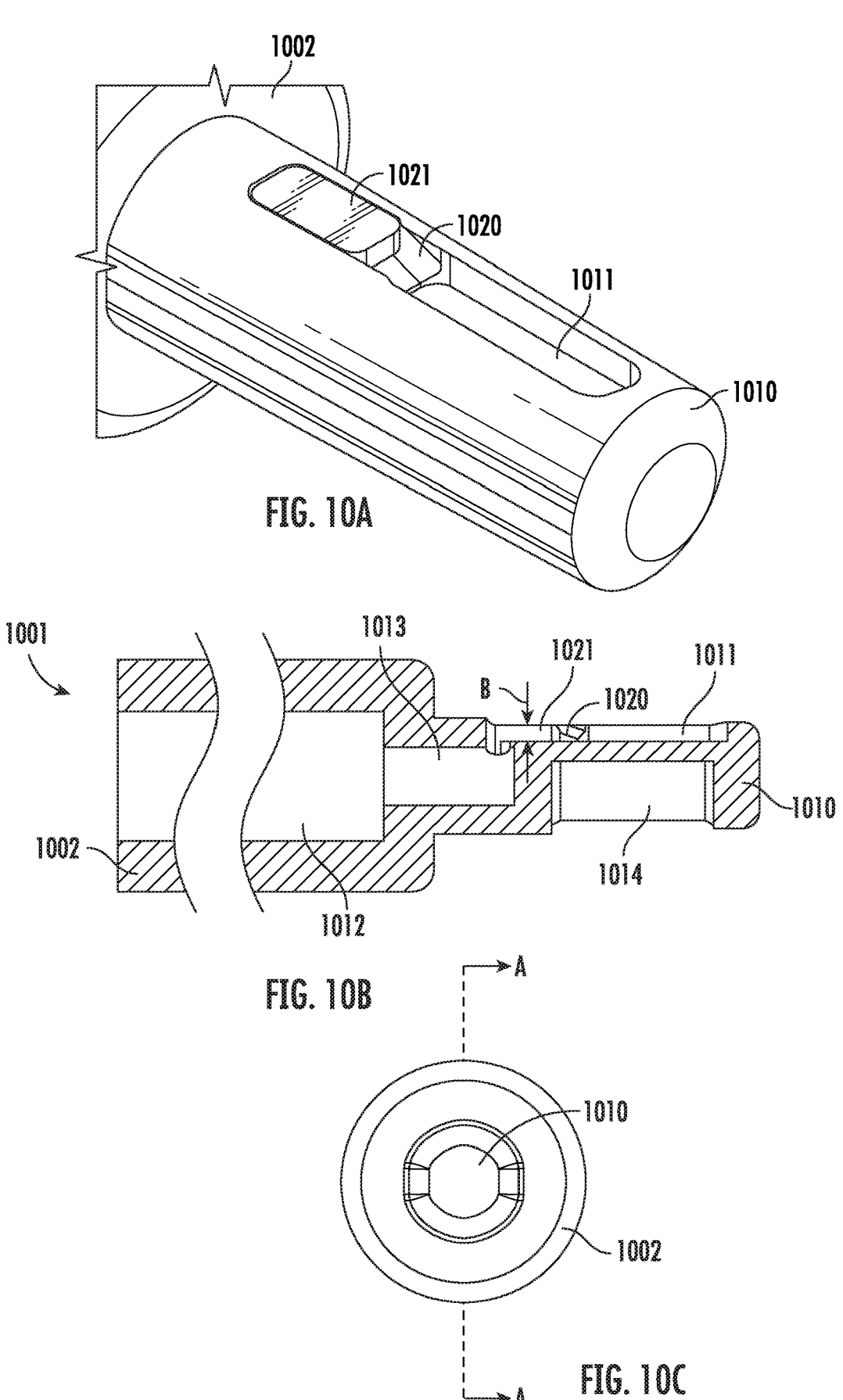
FIG. 10A is a perspective view of a portion of an input portion of a vitrification device according to some embodiments of the present disclosure.
FIG. 10B is a cross-sectional view of the vitrification device of FIG. 10A according to some embodiments of the present disclosure.
FIG. 10C is a front view of the vitrification device of FIG. 10A according to some embodiments of the present disclosure.

FIGS. 10A-10C show an additional embodiment of the vitrification device according to the present disclosure. Particularly, FIG. 10A is a perspective view of partial structures of the device, which shows parts of the handle 1002 and the input portion 1010. The input portion 1010 comprises a sample chamber 1011, a filtering mechanism including a filter 1021, and a ramp 1020 positioned in between the sample chamber 1011 and the filter 1021. FIG. 10B is a cross sectional view of the embodiment as shown in FIG. 10A, taken along the line A-A of FIG. 10C, which shows the input portion 1010 and the handle 1002. Shown in FIG. 10B, the filter 1021 covers a waste channel 1013 which links to a waste reservoir 1012 located in the handle 1002.

In some embodiments, the thickness of the filter 1021 as measured in the distance between arrow pair B of FIG. 10B is in the range of about 0.01 inch to about 0.03 inch. In one example embodiment, the thickness of the filter 1021 is 0.22 inch.

The ramp 1020 connects the sample chamber 1011 with the filter 1021. FIG. 10B shows the vitrification device (without cap) placed horizontally with the sample chamber 1021 facing up. As shown, the ramp 1020 assumes a sloping angle with the surface of the sample chamber 1011 and extends upwardly from one end of the sample chamber 1011. In some embodiments, to collect the waste, a micropipette is used to push the fluids in the sample chamber 1011 to flow across the ramp 1020 and towards the filter 1021. Fluidic waste flows through the filter 1021 into the waste reservoir 1012, while a sample of a larger size is prevented from flowing through. Thus, the sample is retained in the sample chamber. Not intended to be bound by theory, it is also contemplated that the ramp 1020 assists in preventing the sample, such as oocytes or embryo, from attaching to the filter 1021, because gravity acts upon the samples by pulling them down the ramp 1020 and away from the filter 1021.

Alternatively or additionally, in some embodiments, the ramp 1020 forms at least one microfluidic channel, thus providing a capillary wicking power to move a liquid waste from the sample chamber 1011 towards the filter 1021. The capillary action is initiated when a first solution is introduced to the sample chamber 1011 with a fluidic force, such as by using a pipet. The fluid is pushed through the sample chamber 1011, along the ramp 1020, and into the waste reservoir 1012. The presence of fluid in the waste reservoir 1012, in combination with the particularly sized microfluidic channels through the entirety of the device, generates a force strong enough to pull subsequent fluids through the device 1001 using capillary action. Alternatively or additionally, in some embodiments, the filter 1021 is made of an absorptive material, such as a sponge or a filter paper, thus also providing a wicking power that facilitates the removal of a liquid waste out of the sample chamber 1011.

In some embodiments, the filter 1021 selectively lets through the waste into the waste channel 1013, while preventing a sample from passing. For example, in some embodiments, the filter 1021 comprises a mechanism that separates the waste and sample based on their respective sizes. In some embodiments, the mechanism lets through a liquid component but retains a solid component of a mixture. In some embodiments, the filter 1021 has pores that are small enough to block the passage of a solid sample, such as oocytes or embryos. In various embodiments, the size of the pores may vary depending on the type of samples. In some embodiments, the filter 1021 is made of a filtration material. Suitable filtration materials that can be used in connection with the present disclosure include but are not limited to sintered polyethylene beads, polymer mesh, and fibrous paper. In some embodiments, the filtration material prevents sticking of a sample to the filter 1021.

In some embodiments, the vitrification device further has a closed configuration (not shown). In the closed configuration, the cap is placed relative to the input portion such that none of the openings on the cap is in fluidic communication with the sample chamber, and the sample chamber is sealed by the wall of the cap. In some embodiments, in the closed configuration, the one or more recess or opening on the cap is placed in close proximity of the sample chamber. In some embodiments, in the closed configuration, the one or more openings of the cap are in fluidic communication with the recess on the input portion.

The vitrification device in the closed configuration may be submerged into a fluid without exposing the content of the sample chamber directly to the fluid. In some embodiments, the vitrification device is configured for dipping, at least the input portion and cap portions, into liquid nitrogen for vitrification of a sample contained in the sample chamber. In some embodiments, the device is further configured for dipping into a warm medium for thawing of a sample contained therein. In these embodiments, the liquid nitrogen or warm medium can easily get into proximity of the sample, such as through the openings on the cap, but not directly contact the sample when the device is in the closed configuration. In some embodiments, at least the input portion and cap portions of the device are made of a material resistant to liquid nitrogen. In some embodiments, the material is thermal conductive, such that quick vitrification and thawing of the sample may be achieved. Example materials that can be used in connection with the present disclosure include but are not limited to an acrylic-based material, a polypropylene-based material, a polycarbonate-based material and a copolyester-based material.

In some embodiments, switching between the open and closed configurations is achieved by rotating the cap along its longitudinal axis, for example by about 10°, 20°, 30°, 40°, 50°, 60°, 70°, 80°, 90°, 100°, 110°, 120°, 130°, 140°, 150°, 160°, 170°, or 180°. Particularly, referring back to the example embodiment as shown in FIG. 2B, the input port 104 and the openings 107, 108 are located on opposing sides of the cap 103. In this embodiment, switching between the first open configuration and the closed configuration can be achieved by rotating the cap 103 by about 90° around its longitudinal axis, and switching between the first open configuration and the second open configuration can be achieved by rotating the cap 103 by about 180° around its longitudinal axis. In some embodiments, the cap 103 further comprises a grip 106 that facilitates the holding and rotating of the cap.

Figure 11A:
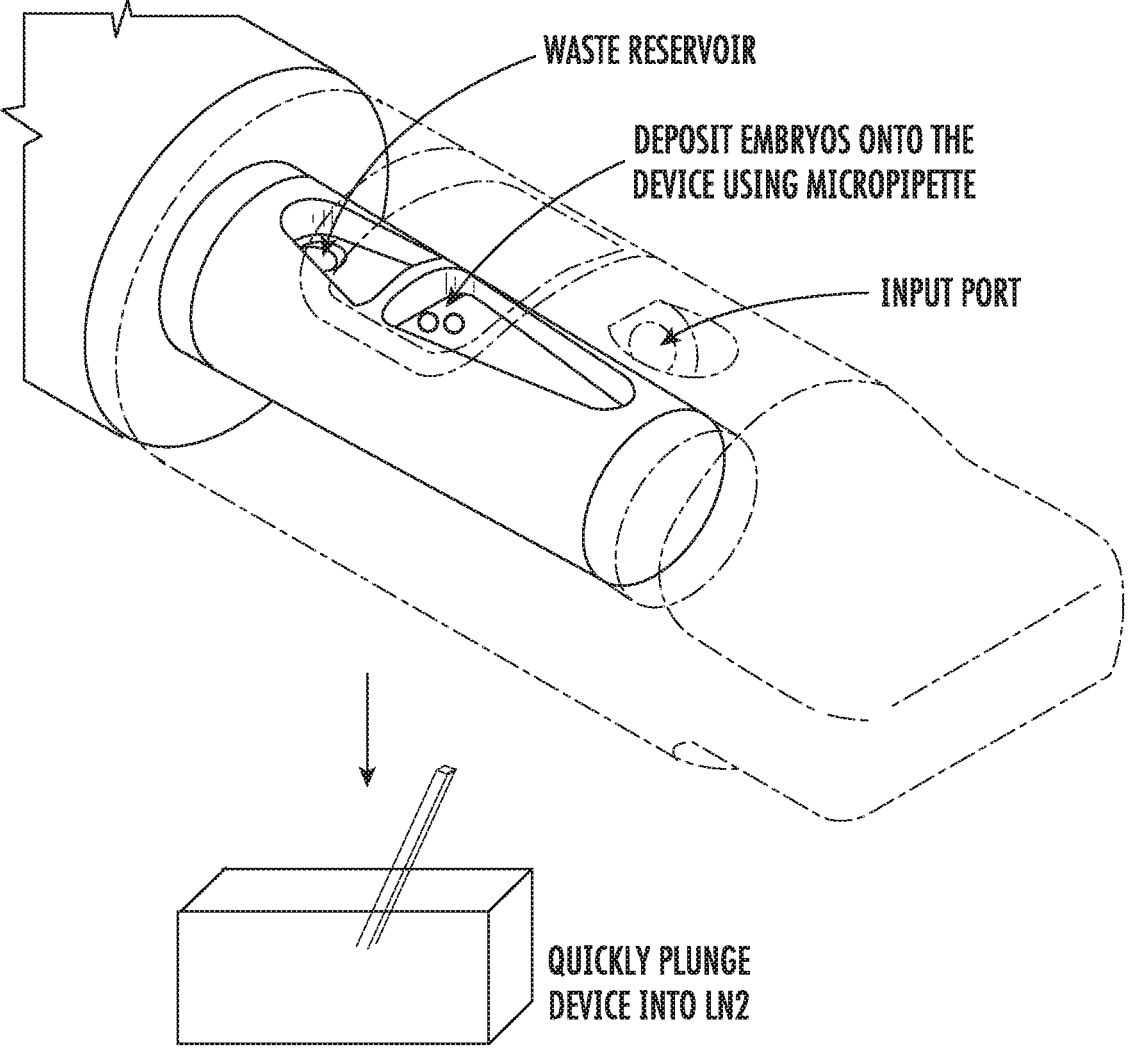
FIG. 11A shows example procedures for freezing an embryo specimen using a vitrification device according to some embodiments of the present disclosure.
Figure 11B:
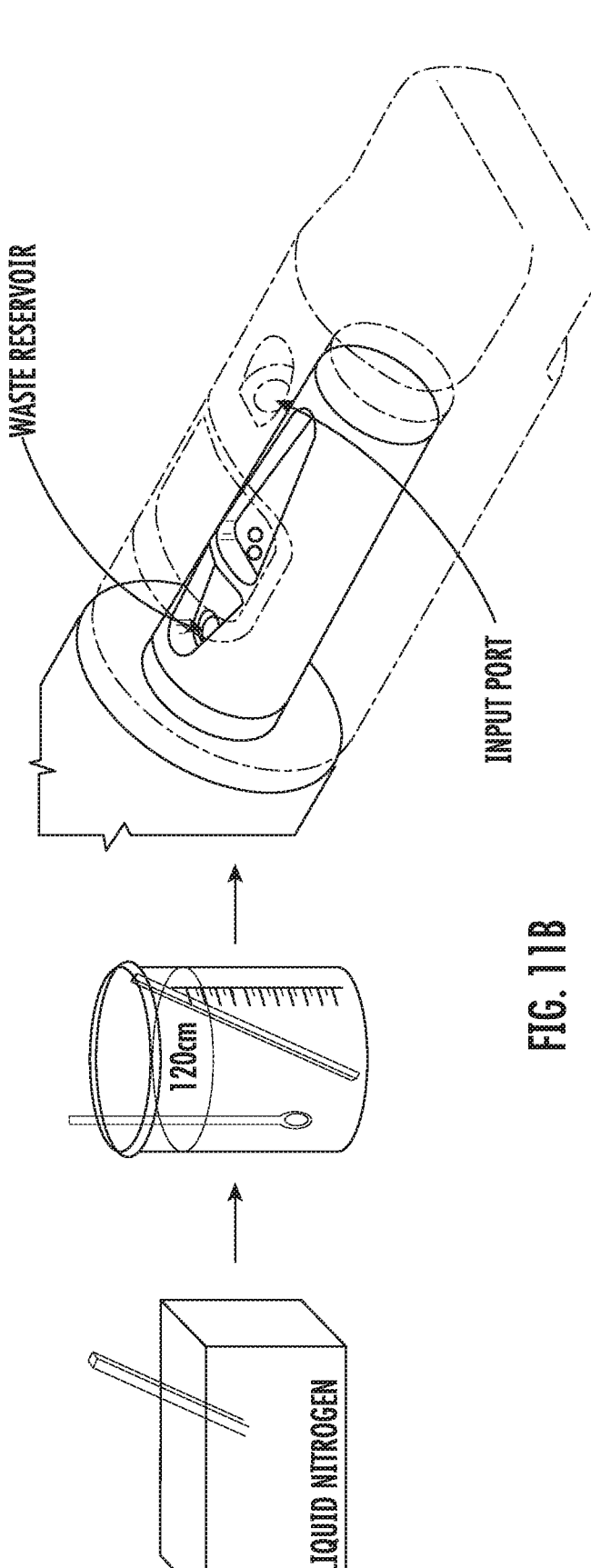
FIG. 11B shows example procedures for thawing an embryo specimen using a vitrification device according to some embodiments of the present disclosure.

FIGS. 11A and 11B illustrate example procedures for freezing and thawing embryos using the present vitrification device. As shown in FIG. 11A, for freezing, the device is first placed in the first open configuration. A culture medium is delivered into the sample chamber through the input port on the cap, followed by delivery of the embryo specimen into the sample chamber. Then a suitable equilibration solution is added through the input port, and the embryos are allowed to equilibrate in the equilibration solution for a period of time before the waste is collected. Afterwards, a vitrification solution is added through the input port, and the embryos are incubated in the vitrification solution for a period of time before the waste is collected. Then the cap is rotated into the closed configuration, and the input portion of the device is quickly plunged into a liquid nitrogen tank for vitrification of the embryos.

As shown in FIG. 11B, for thawing, the frozen device in closed configuration is quickly plunged into a 37° C. warm bath and incubated for a period of time. Then the cap is rotated to the first open configuration. A 37° C. thawing solution is applied through the input port to the sample chamber, and the embryos are allowed to warm for a period of time. Then a room-temperature dilution solution is added, and the embryos are allowed to equilibrate in the dilution solution for a period of time before the waste is collected. Afterwards, a room temperature washing solution is added to the sample chamber, and the embryos are allowed to equilibrate for a period of time before the waste is collected. The washing step may be repeated as needed, before a 37° C. culture medium is added to the sample chamber. Then the cap is rotated to the second open configuration and the embryos are retrieved through an opening on the cap.

It is contemplated that the procedures for freezing and/or thawing a sample using the present device can reduce the number of micropipette manipulations by at least four-fold without compromising the quality of the sample prepared. Further, via the built-in waste collecting mechanism, the amount of solution carry-over in each wet step is reduced and made more consistent from user to user. Thus, advantages of the present device include reducing the risk of damage associated with human manipulation of fragile samples, as well as reducing human error associated with sample preparation, thereby improving consistency of sample quality.

The above freezing and thawing procedures are by way of example only and by no means limit the use of the present vitrification device to the particular examples described. For example, samples that can be used in connection with the present device are not limited to embryo specimens, but also include, for example, oocytes, somatic cells and other suitable sample types. Further, chemical agents to be used to treat the samples are not limited to those described above; rather, it is contemplated that the present device is versatile and can be used with different vitrification kits commercially available. Additionally, the present device may be used for sample processing and preserving outside the context of freezing and thawing. Those of ordinary skill in the art should be able to envisage additional modifications and variations that do not deviate from the principle of the present disclosure, and those modified or varied embodiments are still encompassed by the scope of the present application.

Figures 12A, 12B:
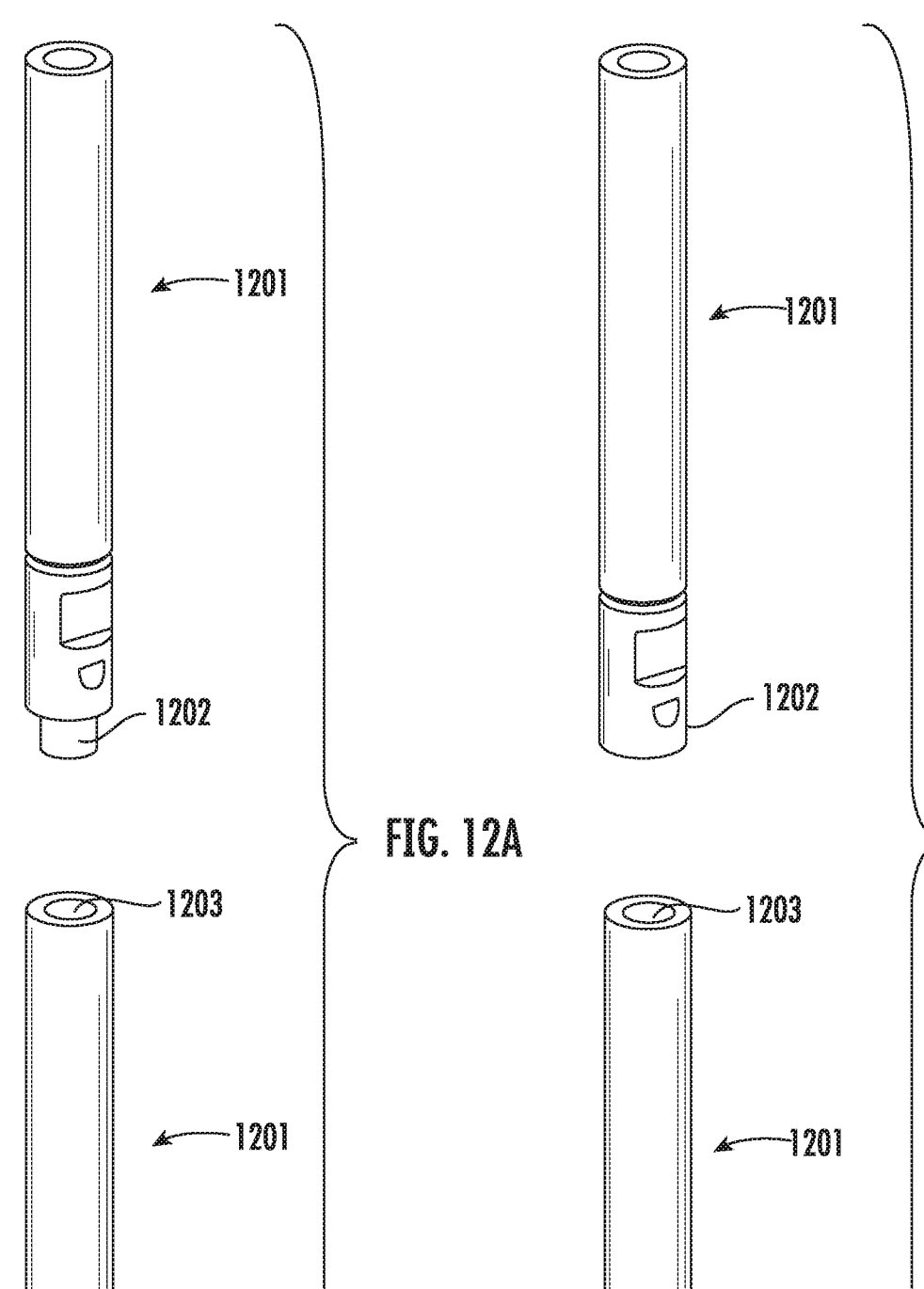
FIGS. 12A-12B illustrate example embodiments for stacking multiple units of the vitrification device according to the present disclosure.

FIG. 12A and FIG. 12B illustrate example embodiments where multiple units of the vitrification device according to the present disclosure may be stacked together, for example, for convenient storage or transportation. FIG. 12A illustrates the example embodiment where each unit of the vitrification device 1201 has a plug 1202 at one end and a receptacle 1203 at the other end. The plug 1202 of one unit engages with the receptacle 1203 of another unit, such that the two units can be stacked together. FIG. 12B illustrates another example embodiment where each unit of the vitrification device 1201 has magnets 1202, 1203 on both ends. The magnets 1202, 1203 engage with each other, thereby stacking multiple units together.

Figure 13A:
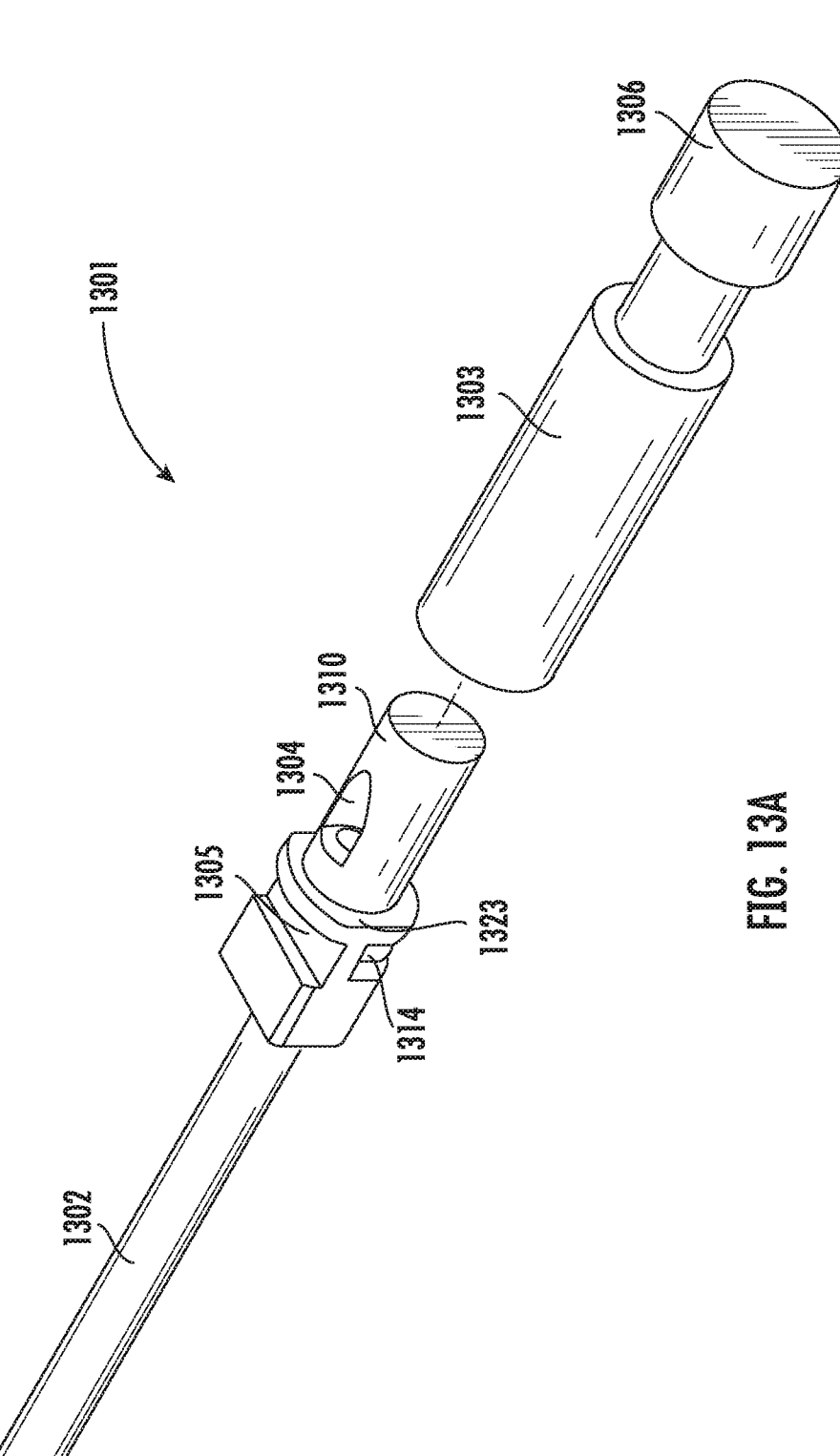
FIG. 13A is a perspective view of a vitrification device according to some embodiments of the present disclosure.

FIG. 13A illustrates an alternative embodiment of the vitrification device according to the present disclosure. As shown, the vitrification device 1301 comprises an elongated member having a handle portion 1302 and an input portion 1310. The input portion 1310 can be reversibly coupled to a cap 1303. In some embodiments, the input portion 1310 is cylindrical and can engage with a cylindrical hollow space within the cap 1303. In some embodiments, the input portion 1310 is tapered, having a larger dimension at the end proximal to the handle 1302 and a smaller dimension at the end distal to the handle 1302. In some embodiments, the input portion 1310 is tapered with a draft of about 1° to about 5°. In some embodiments, the hollow space in the cap 1303 is also tapered with a matching draft, such that the tapered shapes of the input portion 1310 and the cap 1303 create a wedging force that helps to engage and/or seal the two parts together. In some embodiments, the input portion 1310 further comprises a cap stopper 1323 for stopping the cap 1303 from moving further towards the input portion 1310, thereby preventing the cap 1303 from covering the viewing window 1305 or the recess 1314. In some embodiments, the cap 1303 further comprises a grip 1306 for easy holding and rotating the cap 1303.

Figures 13B, 14A:
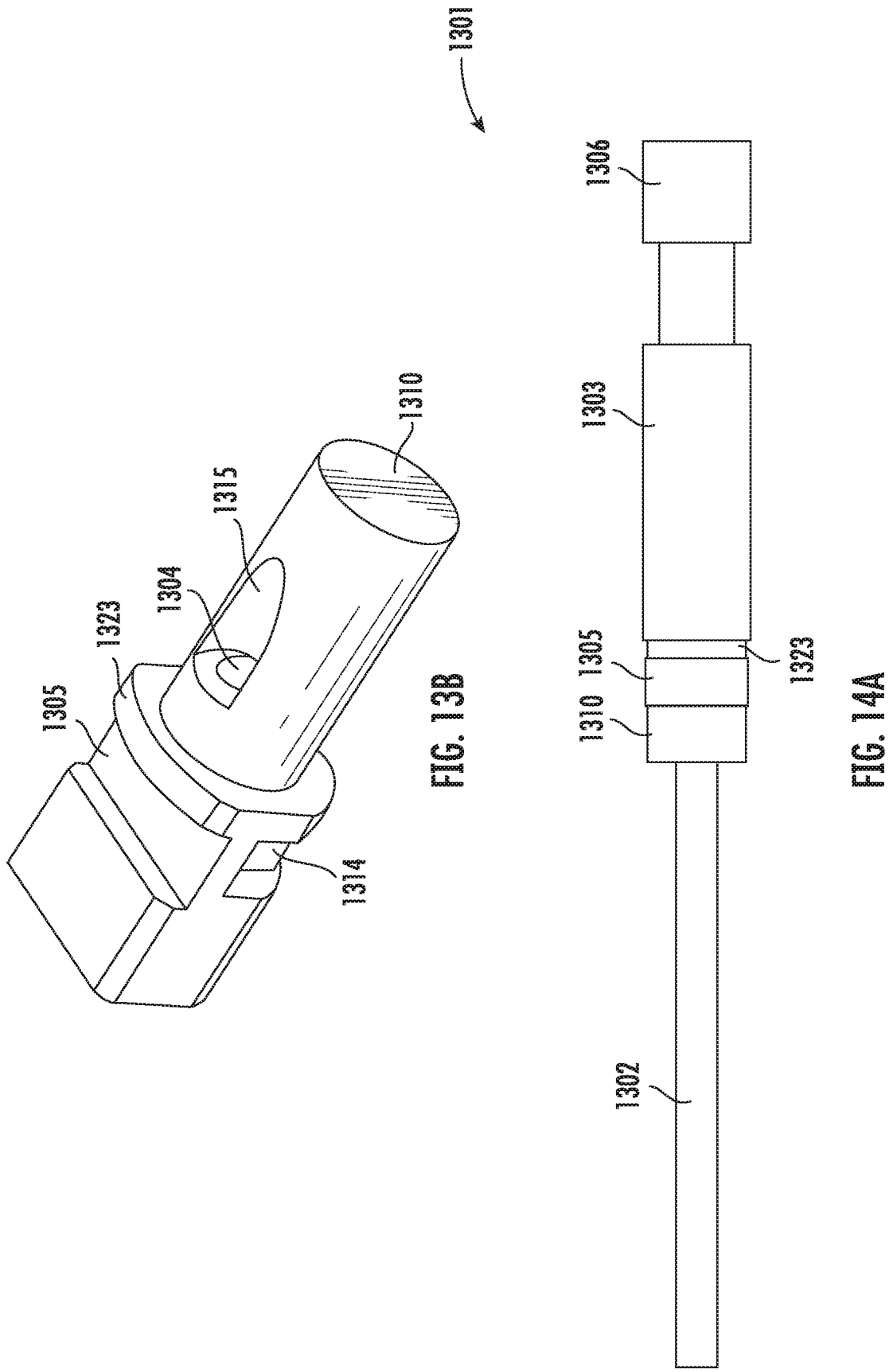
FIG. 13B is a perspective view of an input portion of the vitrification device of FIG. 13A according to some embodiments of the present disclosure.
FIG. 14A is a top view of the vitrification device of FIG. 13A according to some embodiments of the present disclosure with a cap on the input portion.

FIG. 13B is a perspective view of the input portion 1310 of the vitrification device. In some embodiments, the input portion 1310 encloses a sample chamber (not shown) which is in fluidic communication with a waste reservoir (not shown) enclosed within the handle 1302. An input port 1304 connects the sample chamber with the outside. The input portion further comprises a viewing window 1305, and a least a portion of the sample chamber can be visible from the outside through the viewing window 1305. In some embodiments, the input portion 1310 further comprises one or more recess 1314 that are in close proximity to the sample chamber. In some embodiments, when in contact with liquid nitrogen, the recess 1314 allows the liquid nitrogen to get in close proximity to the sample chamber for better vitrification of a sample contained therein. In some embodiments, the input portion 1310 further comprises a recess 1315 next to the opening of the input port 1304. The recess 1315 allows sample-delivering tools, such as a micropipette, to approach the opening of the input port 1304 more easily. The recess 1315 also prevents air from getting into the sample chamber and forming air bubbles when the cap 1303 is pushed onto the input portion 1310.

Figures 14B, 14C:
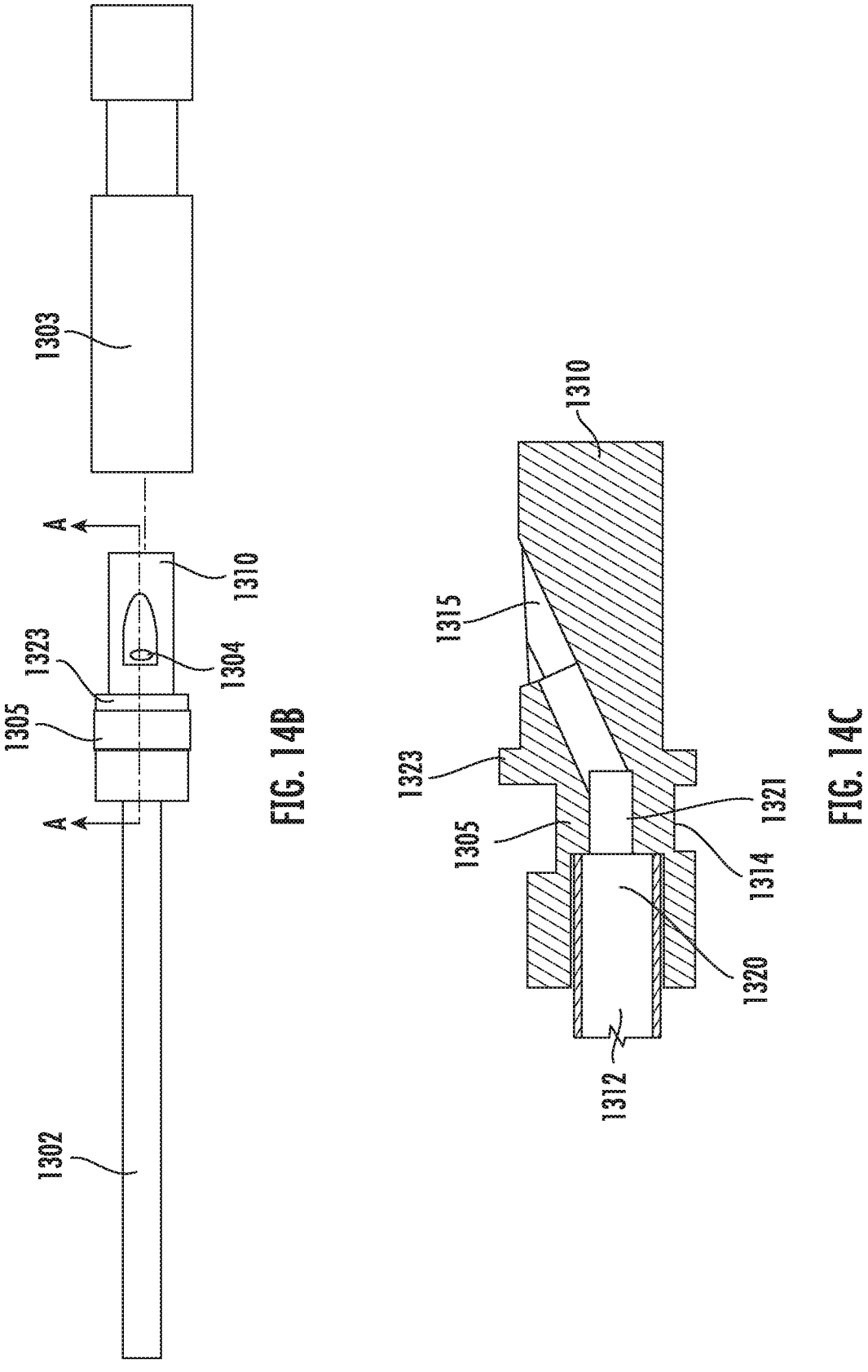
FIG. 14B is a top view of the vitrification device of FIG. 13A according to some embodiments of the present disclosure with the cap removed.
FIG. 14C is a cross-sectional view along line A-A of FIG. 14B.

FIGS. 14A-14D illustrates the vitrification device 1301 showing handle 1302, input portion 1310 and cap 1303. As shown in the top view of FIG. 14A, the portion of the input portion 1310 that is distal to the handle portion 1302 is inserted into the cap 1303. In some embodiments, a cap stopper 1323 helps preventing the cap 1303 from blocking the viewing window 1305. Particularly, in some embodiments, the cap stopper 1303 is located more distal to the handle 1302 than the viewing window 1305. In some embodiments, the cap further comprises a grip 1306 for easy holding and handling of the cap 1303. FIG. 14B also illustrates the top view of the vitrification device 1301. In this view, the cap 1303 is removed from the input portion 1310, and the input port 1304 is exposed.

FIG. 14C illustrates the cross section along the A-A line of FIG. 14B. As shown, the input portion 1310 comprises a sample chamber 1311, which is connected with the outside through the input port 1304. The sample chamber 1311 comprises at least one surface 1321 where a sample can be deposited. The viewing window 1305 lays over the sample chamber 1311, such that the content and/or activity within the sample chamber 1311 can be visible from the outside. The recess 1314 is in close proximity to the sample chamber 1311. In this example embodiment, the sample chamber 1311 and the recess 1314 are separated by a thin wall that allows faster thermal transfer, for example, between a sample in the sample chamber 1311 and liquid nitrogen in the recess 1314. In some embodiments, the input portion 1310 further comprises a recess 1315 next to the opening of the input port 1304.

The sample chamber 1311 is in fluidic communication with a waste reservoir 1312, which extends into the handle 1302 portion of the device. A filtering mechanism 1320 sits in between the sample chamber 1311 and the waste reservoir 1312. In some embodiments, the filtering mechanism 1320 selectively lets through a waste into the waste reservoir 1312, while retaining the sample within the sample chamber 1311. In some embodiments, the filtering mechanism 1320 separates the waste and sample based on their respective sizes. In some embodiments, the filtering mechanism 1320 lets through a liquid component but retains a solid component of a mixture. In some embodiments, the filtering mechanism 1320 has pores that are small enough to block the passage of a solid sample, such as oocytes or embryos. In various embodiments, the size of the pores may vary depending on the type of samples.

In some embodiments, the filtering mechanism 1320 is a mesh. In some embodiments, the holes through the mesh are small enough to allow a wicking power to draw the fluid via capillary action. In some embodiments, when in use, a fluidic pressure is first provided in the sample chamber 1311 to push a liquid through the mesh. The presence of fluid in the waste reservoir 1312 generates a force strong enough to pull subsequent fluids through the device 1301 using capillary action. Furthermore, liquid flowing through the mesh to wet the holes may add to the wicking power to move the liquid and/or subsequent additional liquids through the mesh even without the fluidic pressure. According to the present disclosure, materials suitable for the filtering mechanism 1320 include but are not limited to sintered polyethylene beads, polymer mesh, and fibrous paper. In some embodiments, the material has a smooth surface and prevents sticking or attachment of a sample.

Figure 14D:
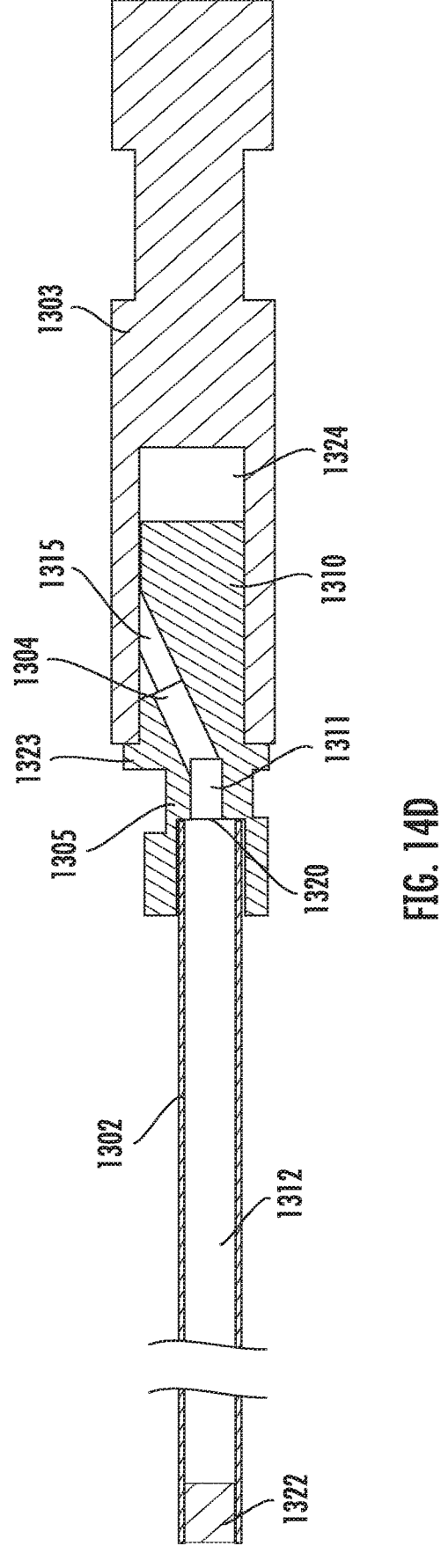
FIG. 14D is a cross-sectional view of the vitrification device of FIG. 13A according to some embodiments of the present disclosure.

FIG. 14D shows the cross sectional view of the whole device. The cap 1303 has an internal hollow space 1324 for housing the input portion 1310. In some embodiments, when the cap 1303 is coupled to the input portion 1310, the input port 1304 is sealed. An air pocket forms in the recess 1315 when the cap 1303 is pushed onto the input portion 1310. Thus the recess 1315 prevents air from being pushed into the input port 1304 and forming bubbles in the sample chamber 1311 when the cap 1303 is coupled to the input portion 1310. In some embodiments, the input portion 1310 further comprises a cap stopper 1323 for preventing the cap 1303 from blocking the viewing window 1305. In some embodiments, the device further comprises a mechanism that prevents the waste from moving from the waste reservoir 1312 back into the sample chamber 1311. In some embodiments, the device further comprises a mechanism, such as a filter 1322, that allows air in the waste reservoir 1312 to vent as waste enters, and prevents liquid nitrogen from entering the waste reservoir 1312. In some embodiments, the filter 1322 also prevents a liquid waste from leaking out of the waste reservoir

1312. In some embodiments, the filter 1322 has a pore size that is small enough to prevent liquid from passing through but large enough to allow air to pass. In some embodiments, the filter 1322 has a pore size of about 20 microns. In some embodiments, the filter 1322 is made of from PTFE, polyethylene or polypropylene.

Figure 15A:
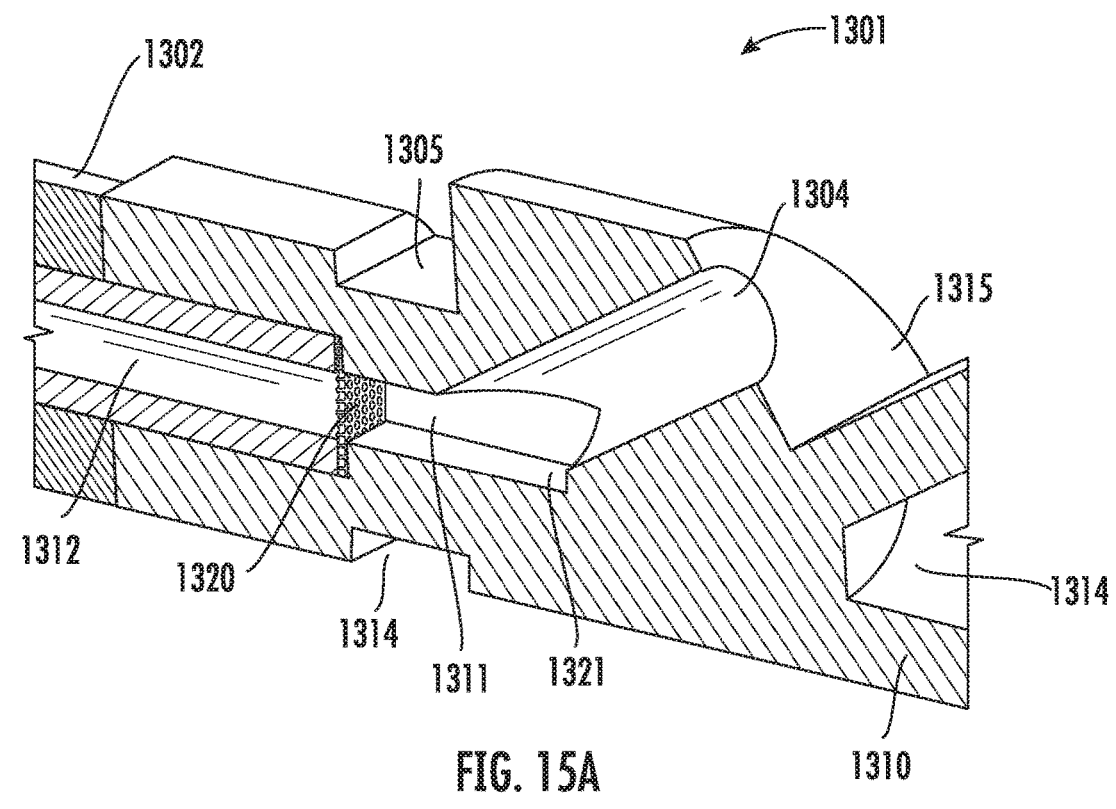
FIG. 15A is a partial cross-sectional view of the vitrification device of FIG. 13A according to some embodiments of the present disclosure.
Figure 15B:
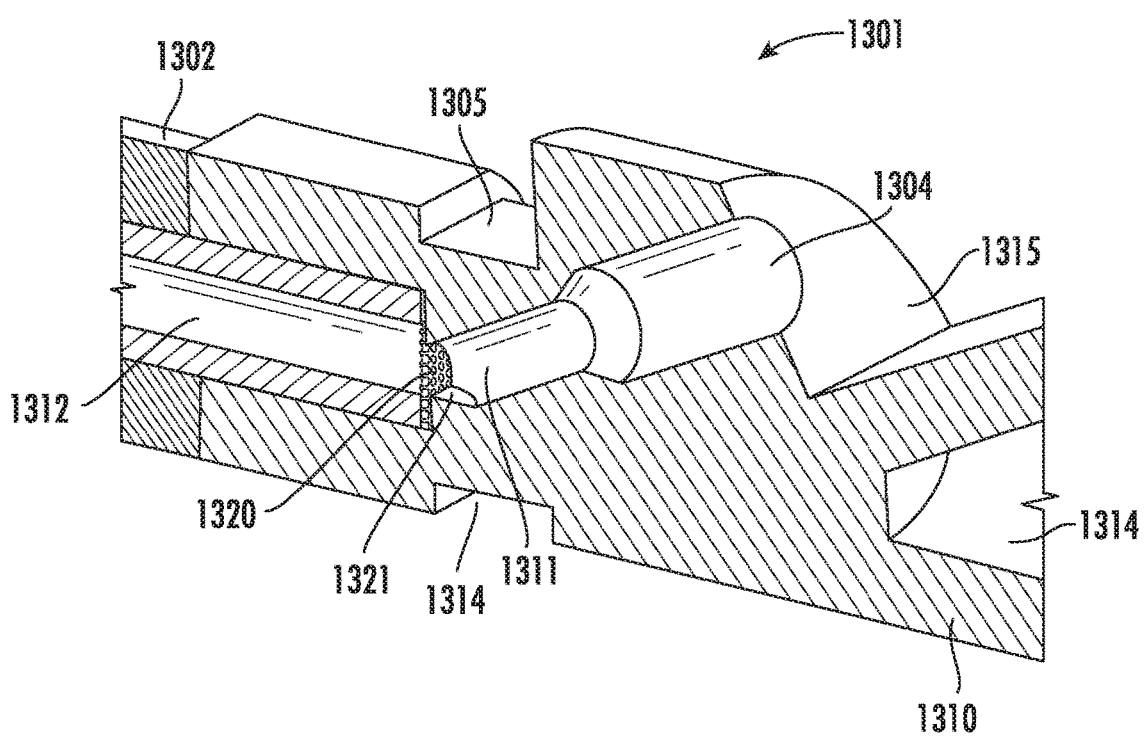
FIG. 15B is a partial cross-sectional view of the vitrification device of FIG. 13A according to some embodiments of the present disclosure.

FIGS. 15A and 15B illustrate alternative embodiments of the vitrification device 1301 in a perspective view. A cross section along the longitudinal axis of the device is also shown. Particularly, shown in FIG. 15A is a partial structure of the vitrification device 1301, including handle 1302 (partially shown) and input portion 1310 (partially shown). The input portion 1310 comprises a sample chamber 1311. An input port 1304 connects the sample chamber 1311 with the outside. The input portion 1310 further comprises a waste reservoir 1312 that extends into the handle 1302. In this example embodiment, a filtering mechanism 1320, such as a mesh, is positioned between the sample chamber 1311 and the waste reservoir 1312. A viewing window 1305 lays over the sample chamber 1311, such that a user may see the contents and/or activities within the sample chamber 1311 through the viewing window 1305. The input portion 1310 further comprises at least two recesses 1314 in close proximity of the sample chamber 1311. When in contact with liquid nitrogen, the recesses 1314 allow liquid nitrogen to get into the proximity of the sample chamber 1311 for better vitrification effect. When the cap (not shown) engages with the input portion 1310, the input port 1304 is sealed. In some embodiments, the input portion 1310 further comprises a recess 1315 near the opening of the input port 1304. The recess 1315 allows sample-delivering tools, such as a micropipette, to approach the opening of the input port 1304 more easily. The recess 1315 also prevents air from getting into the sample chamber 1311 and forming air bubbles when the cap is pushed onto the input portion 1310.

As shown in FIG. 15A, the sample chamber 1311 has at least a surface 1321 where a sample may be disposed. The sample-receiving surface 1321 may assume an angle with the input port 1304 for easy delivery of the sample onto the surface 1321. In some embodiments, the angle between the input port 1304 and the sample-receiving surface 1321 in the range of about 20° to about 70°. According to the present disclosure, the dimensions of the sample-receiving surface 1321 and the input port 1304 are not critical as long as a sample can be easily delivered. FIG. 15B shows an alternative embodiment where the area of the sample receiving surface 1321 is reduced. In this example embodiment, the input port 1304 has two segments. The first segment next to the opening of the input port 1304 has a larger diameter compared to the second segment next to the sample chamber. In other embodiments, the input port 1304 may be tapered, with a larger dimension at the opening, and a smaller dimension towards the sample chamber 1311.

Figure 16:
FIG. 16 is a top perspective view of a vitrification device according to some embodiments of the present disclosure.

FIGS. 16-21 illustrate an alternative embodiment of a vitrification device according to the present disclosure. FIG. 16 is a perspective view of the vitrification device 1601. The vitrification device 1601 comprises an elongated shape with two ends. On one end, the device 1601 comprises an input portion (not shown) that is able to be reversibly coupled to a removable cap 1603. In some embodiments, the input portion 1610 is cylindrical and can engage with a cylindrical hollow space within the cap 1603. The device further includes a handle portion 1602 and a cap 1630 at the second end. The device 1601 also includes at least one viewing window 1605. The vitrification device has a closed configuration (shown in FIG. 16) and an open configuration (shown in FIGS. 18-19). Switching to the closed and open configurations is achieved by coupling or uncoupling, respectively, the cap 1603 to the input portion 1610. In the embodiment shown, the cap 1603 has a plurality of ridges forming a grip for easy holding and handling of the cap 1603.

Figure 17:
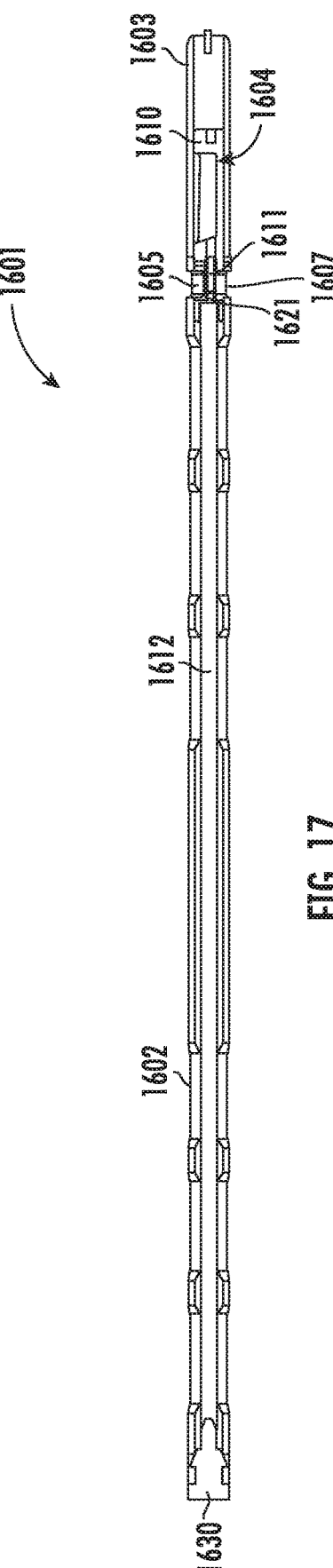
FIG. 17 is a cross-sectional view of the vitrification device of FIG. 16 according to some embodiments of the present disclosure.

FIG. 17 is a longitudinal cross-section view of the vitrification device 1601 in the closed configuration with cap 1603 coupled to the input portion 1610. In this configuration, the input port 1604 and, thus, the sample chamber 1611 is sealed by the wall of the cap 1603. The vitrification device 1601 in the closed configuration may be submerged into a fluid without exposing the content of the sample chamber 1611 directly to the fluid, as described above.

When in the open configuration, the input port 1604 is configured to receive a sample and fluidic agents for delivery to the sample chamber 1611. The input port 1604 is in fluidic communication with the sample chamber 1611, which is also in fluidic communication with a waste reservoir 1612 through a filtering mechanism including a filter 1621. The viewing window 1605 is located in the area around the sample chamber 1611. An opening 1607 is formed in the handle portion 1602 diametrically opposite of the viewing window 1605.

Figure 18:
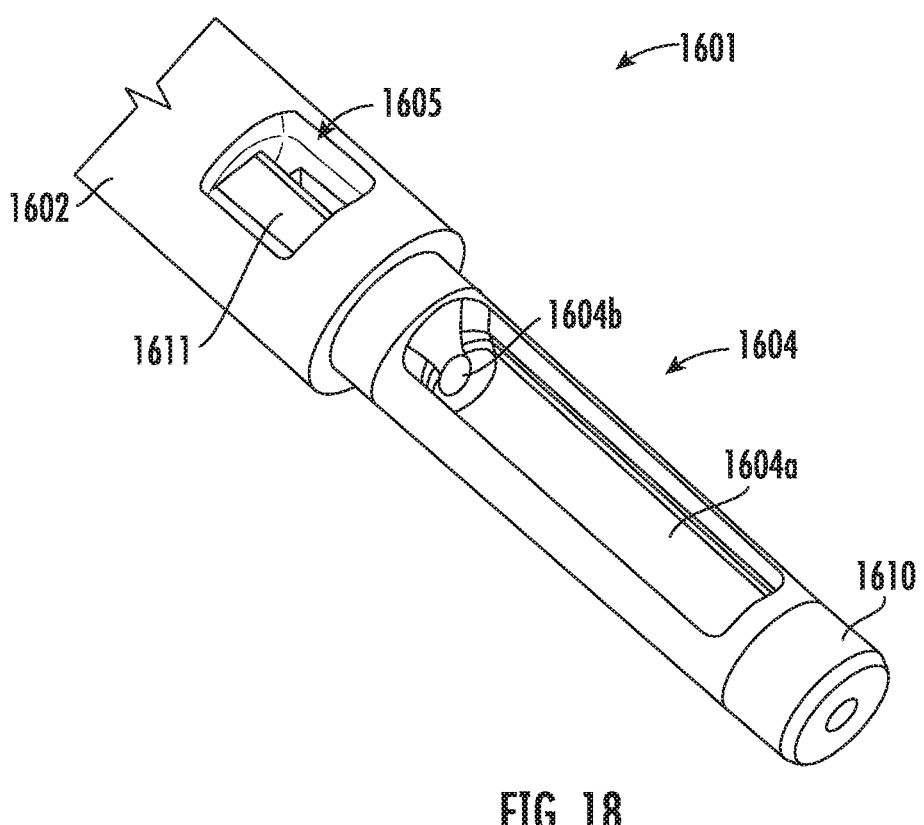
FIG. 18 is a perspective view of an input portion of the vitrification device of FIG. 16 according to some embodiments of the present disclosure.

FIG. 18 illustrates the input portion 1610 and a portion of the handle 1602 of the vitrification device 1601. The vitrification device 1601 is shown in the open configuration (the cap 1603 is removed), such that the input port 1604 is exposed. The input port 1604 comprises a trough-like recess 1604a in the wall of the input portion 1610 and an input channel 1604b which leads to the sample chamber 1611. The recess 1604a allows sample-delivering tools, such as a micropipette, to approach the opening of the input channel 1604b more easily. Fluidic agents delivered by way of the recess 1604a flow through the input channel 1604b directly to a sample in the sample chamber 1611.

The viewing window 1605 allows a user of the device to view and examine the conditions of a sample located within the sample chamber 1611. In some embodiments, the viewing window 1605 may be formed by an opening in the wall, such that an outside wall of the sample chamber 1611 is exposed. In other embodiments, the viewing window 1605 is made of a transparent material, such that a user of the device can easily see through to examine the conditions of a sample located within the sample chamber 1611. In various embodiments, the viewing window 1605 can be made of the same or a different material as the remaining parts of the device 1601. The sample chamber 1611 is enclosed by a transparent material to allow for viewing of the sample in the chamber. In some embodiments, the wall of the sample chamber 1611 is less than 0.005 inches, and preferably less than or equal to 0.002 inches which allows for the sample to thaw at the preferred rate.

Figure 19:
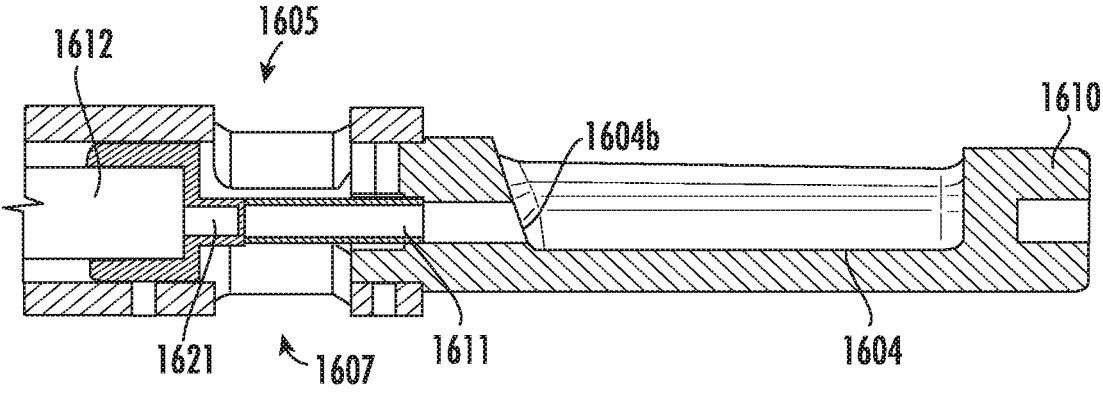
FIG. 19 is a cross-sectional view of the portion of the input portion shown in FIG. 18 according to some embodiments of the present disclosure.

FIG. 19 is a cross-sectional view of the input portion 1610 and portion of the handle 1602 shown in FIG. 18. In this view, there is shown an opening 1607 diametrically opposite of the viewing window 1605. The opening 1607 exposes the space surrounding the sample chamber 1611. When the input portion 1610 is submerged in liquid nitrogen, for example, the liquid nitrogen flows through the opening 1607 and into proximity of the sample in the sample chamber 1611. In some embodiments, the number of such openings is not limited to one. In various embodiments, the viewing window 1605 also serves as an opening in a similar fashion. It is contemplated that in some embodiments, having at least two openings allows fast flowing of liquid nitrogen to the proximity of the sample area and thus fast vitrification of the sample, as air trapped in the space surrounding the sample chamber 1611 can escape through one opening while liquid nitrogen enters through another.

A user may deliver a fluidic agent, such as a sample or solutions for preparing or treating the sample, into the sample chamber 1611 through the input port 1604, while monitoring contents and/or activities within the sample chamber 1611 through the viewing window 1605. Waste is then collected into the waste reservoir 1612. In various embodiments, the device 1601 comprises a mechanism, such as a filtering mechanism, for retaining the sample while letting through waste to reach the waste reservoir 1612. For example, in this embodiment, filter 1621 separates the sample chamber 1611 from the waste reservoir 1612.

Figure 20:
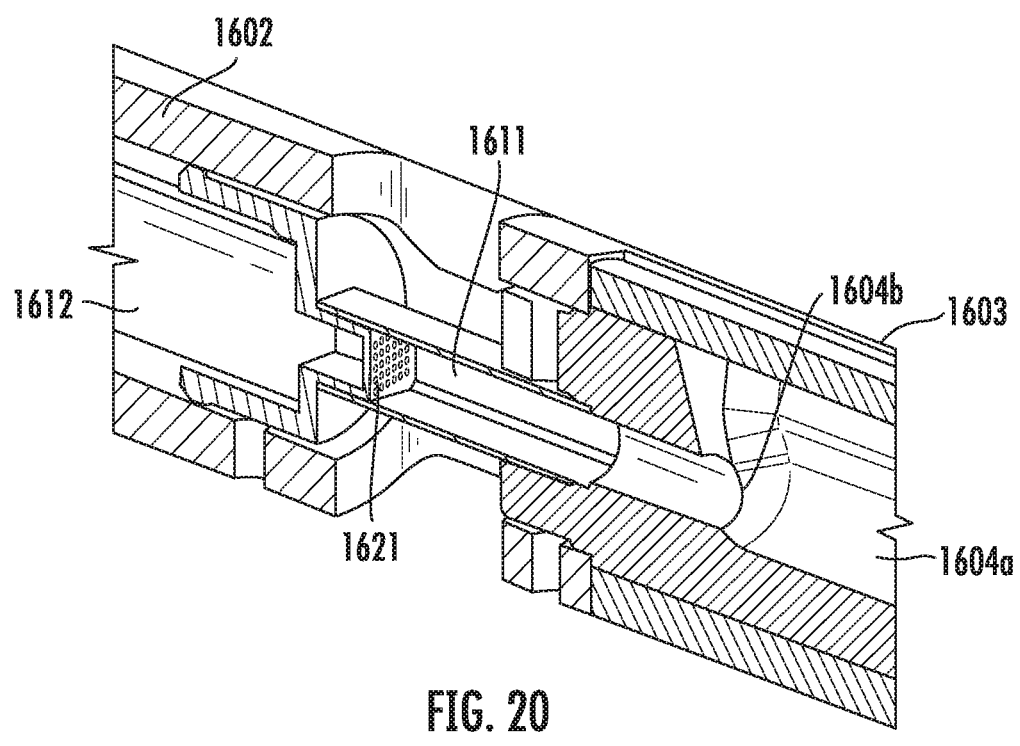
FIG. 20 is a cross-sectional view of a portion of the vitrification device of FIG. 16 according to some embodiments of the present disclosure.

The filter 1621 is shown in detail in the perspective cross-sectional view of FIG. 20. In some embodiments, the filter 1621 selectively allows the waste to flow into the waste reservoir 1612, while preventing a sample from passing. For example, in some embodiments, the filter 1621 comprises a filtration mechanism that separates the waste and sample based on their respective sizes. In some embodiments, the filtration mechanism lets through a liquid component but retains a solid component of a mixture. Thus, the sample is retained in the sample chamber 1611. In some embodiments, the filter 1621 has pores that are small enough to block the passage of a solid sample, such as oocytes or embryos. In various embodiments, the size of the pores may vary depending on the type of samples. In some embodiments, the filter 1621 has a plurality of pores, for example, laser drilled holes in an injection molded component. The size, number, and/or arrangement of the pores is selected to promote capillary action (described below). In some embodiments, the filter 1621 component includes a 7×9 array of pores having a diameter of approximately 0.002 inch with 0.003 spacing between the centers of the pores. In other embodiments, the filter 1621 may have a different number of pores in the array, pores of a different diameter, and/or a different spacing between the pores.

In other embodiments, the filter 1621 is made of a filtration material. Suitable filtration materials that can be used in connection with the present disclosure include but are not limited to sintered polyethylene beads, polymer mesh, and fibrous paper. In some embodiments, the filtration material prevents sticking of a sample to the filter 1621.

Vitrification device 1601 is sized and configured to draw fluid from the input port 1604 through the filtering mechanism and into the waste reservoir 1612 via capillary action. In this way, sample fluids flow from the input port 1604, through the sample chamber 1611, and into the waste reservoir 1612 without the assistance of, or even in opposition to external forces. In some embodiments, the small passageways through the input port 1604, sample chamber 1611, the pores in the filter 1621, and/or the waste reservoir 1612 form microfluidic channels, thus providing a capillary wicking power to move a liquid waste from the sample chamber 1611 towards the filter 1621. The capillary action is initiated when a first solution is introduced through the input port 1604 with a fluidic force, such as by using a pipet. The fluid is pushed through the sample chamber 1611, past the pores of the filter 1621, and into the waste reservoir 1612. The presence of fluid in the waste reservoir 1612, in combination with the particularly sized microfluidic channels through the entirety of the device, generates a force strong enough to pull subsequent fluids through the device 1621 using capillary action. Additionally, in some embodiments, the filter 1621 is made of an absorptive material, such as a sponge, a filter paper, or a mesh which when wetted also provides a wicking power that facilitates the removal of a liquid waste out of the sample chamber 1611. In some embodiments, once a liquid flows through the material and wets the holes, capillary action starts and the wicking power assists with moving the liquid and/or subsequent additional liquids through the material even without the fluidic pressure.

Figure 21:
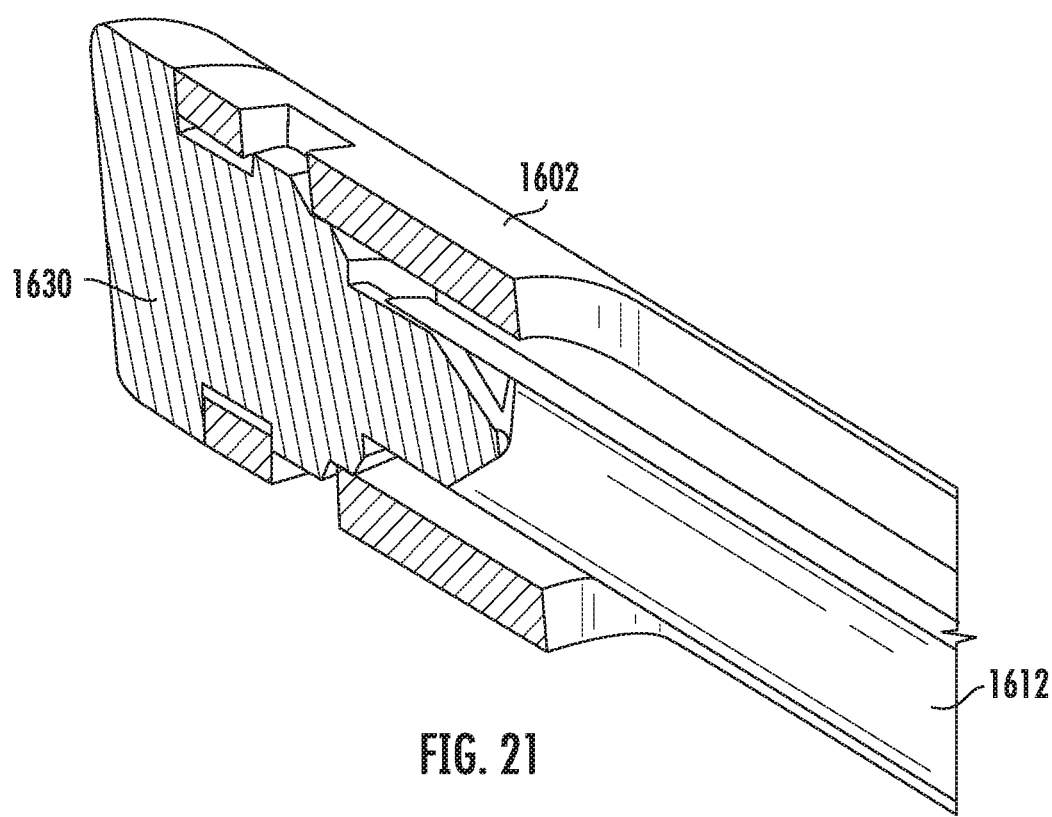
FIG. 21 is a cross-sectional view of a portion of the vitrification device of FIG. 16 according to some embodiments of the present disclosure.

Liquid waste is collected in the waste reservoir 1612 which is contained in the handle portion 1602. In some embodiments, the waste reservoir is sized and configured to have the capacity to hold all waste fluids used during pre-treating and preparing a sample for vitrification, such that the waste reservoir 1612 does not reach maximum capacity and does not need to be emptied. The waste reservoir 1612 has a cap 1630 at the end opposite of the input portion 1610, as shown in FIG. 21, which allows the reservoir to vent as fluid is pulled in from the sample chamber 1611. Furthermore, the cap 1630 helps to maintain the position of the waste reservoir 1612 in the axial centerline of the device 1601 to provide equal clearance around the waste reservoir 1612 for liquid nitrogen (for freezing) and warm water (for thawing) to pass around the waste reservoir 1612. In some embodiments, the cap 1630 provides a unique color identifier to the user by being molded in multiple colors; unique for various sizes, uses, etc. of the device 1621.

The device 1621 is further configured to seal the sample chamber 1611 for submersion in liquid nitrogen. Particularly, the cap 1603 seals the input portion 1610 end of the device 1621 and the other end is sealed by way of frozen solution in the waste reservoir 1612 which acts as a plug.

FIGS. 22A-22D depict alternative embodiments of the input portion 1610 of the vitrification device 1601. As shown in these figures, the input portion 1610 includes input port 1604 having various design features for preventing or limiting the passage of air bubbles into the specimen chamber 1611 during freezing or thawing of the sample. When the cap 1603 is placed onto the device 1621 after the solutions have been introduced, a bubble forms under the cap 1603 as the liquid level goes below the top of the input port 1604. As a result, the bubble gets pushed toward the opening of the input channel 1604b. An air bubble may damage the sample in the sample chamber 1611, therefore, the features of FIGS. 22A-22D assist with limiting potential damage to the sample.

Figures 22A, 22B:
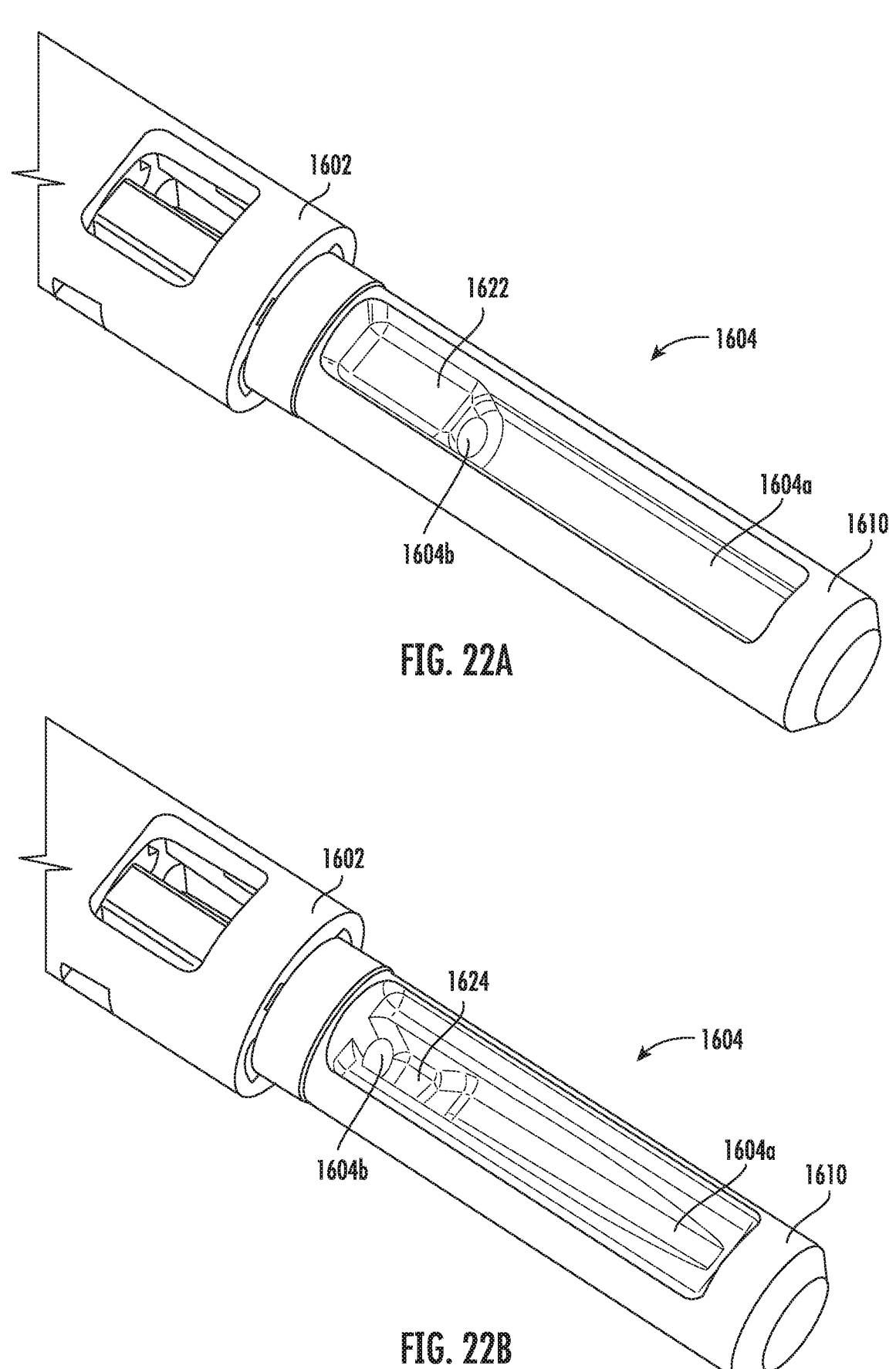
FIGS. 22A-22D are perspective views of alternative embodiments of an input portion of the vitrification device of FIG. 16 according to some embodiments of the present disclosure.

In FIG. 22A, the input port 1604 has the opening to the input channel 1604b separated from the end of the input recess 1604a by raised portion 1622. When the cap (not shown) is placed onto the input portion 1610, any bubble that has formed will remain above the input channel 1604b on top of the raised portion 1622. Once frozen, the contraction of the frozen liquid will not be able to suck the bubble into the chamber. Therefore, once thawed, the chamber will remain bubble free.

In FIG. 22B, the input port 1604 includes portions at different elevations with respect to the opening of the input channel 1604b. The second recessed portion 1624 is lower than the input port recess 1604a, but is higher in elevation relative to the opening of the input channel 1604b. In this way, the fluid level remains above the second recessed portion 1624 (and above the opening to the input channel 1604b) with a smaller quantity of liquid. The ramp portion separating the input port recess 1604a and the second recessed portion 1624 helps to maintain the fluid level above the opening of the input channel 1604b. In this way, the thawing process may be faster than if the entire recess 1604a depth is the same, requiring a large quantity of fluid to thaw. Thawing would take more time, which may jeopardize specimen viability.

Figures 22C, 22D:

Regarding FIGS. 22C-22D, the input port recess 1604a includes a narrow portion 1626. The bubble, which is as wide as the port recess 1604a, cannot be squeezed through the narrow portion 1626. Therefore, the bubble is kept away from the opening of the input channel 1604b. Furthermore, in FIG. 22C, the input recess 1604a is slanted, which allows for use of a minimal amount of fluid present in the recess 1604a while still ensuring that the liquid level does not drop too low (i.e., remains above the opening to the input channel 1604b). Having less liquid to thaw allows warm solution to reach the specimen faster, which promotes viability of the specimen.

In FIG. 22D, there is a trough 1628 within the input recess 1604a. The trough 1628 provides a passage way for liquid which allows flow, even if there is a bubble trapped near the opening to the input channel 1604b after thaw. It is intended that the trough 1628 will always be filled with liquid. Therefore, by having a passage way for liquid to flow, even when there is bubble formation, there will still be liquid movement, which is very important during thawing of the specimen. If a bubble becomes an obstruction to the flow path, the specimen viability will be compromised.

In some embodiments, at least the input portion and cap portions of the device are made of a material resistant to liquid nitrogen. In some embodiments, the material is thermal conductive, such that quick vitrification and thawing of the sample may be achieved. Example materials that can be used in connection with the present disclosure include but are not limited to an acrylic-based material, a polypropylene-based material, a polycarbonate-based material and a copolyester-based material.

The vitrification devices described above in accordance with the various disclosed embodiments include similar features and operate according to similar principles, and like reference numerals refer to like elements. It should be understood that certain components or details may be omitted from the descriptions of certain embodiments, but similar elements may perform the same functionality or include the same features as described above in connection with other embodiments of the vitrification device.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely examples and that equivalents of such are known in the art.

What is claimed is:

1. A vitrification device comprising:
an input portion with an input port;
a sample chamber coupled to the input port, wherein the sample chamber comprises a magnet configured to engage a magnet of an additional vitrification device;
a waste reservoir coupled to the sample chamber and in fluid communication with the sample chamber such that the sample chamber is between the input port and the waste reservoir; and
a filtering mechanism positioned between the sample chamber and the waste reservoir such that the filtering mechanism is arranged to retain a sample within the sample chamber while allowing a fluid introduced through the input port to pass through the sample chamber, across the filtering mechanism, and into the waste reservoir;
wherein the sample chamber, waste reservoir, and filtering mechanism are configured to draw fluid from the sample chamber through the filtering mechanism and into the waste reservoir via capillary action.

2. The vitrification device of claim 1, further comprising at least one viewing window incorporated as a part of the sample chamber, where the at least one viewing window is constructed of different material than a remainder of the sample chamber, wherein the at least one viewing window is configured such that the sample within the sample chamber is viewable through the at least one viewing window.

3. The vitrification device of claim 1, further comprising a cap coupled to the input portion and rotatable around an axis of the input portion between a closed configuration in which the cap seals the input port so as to inhibit flow of fluid within the vitrification device and an open configuration in which fluid can be provided to the sample chamber through the input port.

4. The vitrification device of claim 1, wherein the filtering mechanism comprises a filtration grate comprising a plurality of alternating lower and taller segments thereby forming, at the lower segments, a plurality of microfluidic channels for promoting capillary action.

5. The vitrification device of claim 1, wherein the sample chamber is formed of at least one of: an acrylic-based material, a polypropylene-based material, a polycarbonate-based material and a copolyester-based material.

6. The vitrification device of claim 1, wherein the sample chamber has a wall with a thickness less than or equal to 0.002 inches.

7. The vitrification device of claim 1, further comprising a handle coupled to the input portion, wherein the waste reservoir is positioned in the handle.

8. The vitrification device of claim 1, wherein a fluid capacity of the waste reservoir is sized to hold all waste fluids resulting from use of the vitrification device for treating and preparing the sample for vitrification without emptying the waste reservoir.

9. The vitrification device of claim 1, further comprising a filter coupled to the waste reservoir and configured to allow air to vent from the waste reservoir such that the fluid can flow into the waste reservoir concurrently with retention of the fluid in the waste reservoir.

10. A vitrification device comprising:
an input portion with an input port;
a sample chamber coupled to the input port:
a waste reservoir coupled to the sample chamber and in fluid communication with the sample chamber such that the sample chamber is between the input port and the waste reservoir; and
a filtering mechanism positioned between the sample chamber and the waste reservoir such that the filtering mechanism is arranged to retain a sample within the sample chamber while allowing a fluid introduced through the input port to pass through the sample chamber, across the filtering mechanism and into the waste reservoir;
wherein the sample chamber, waste reservoir, and filtering mechanism are configured to draw fluid from the sample chamber through the filtering mechanism and into the waste reservoir via capillary action;
wherein the filtering mechanism comprises a filtration grate positioned on an island between the sample chamber and an input portion of the waste reservoir, the island comprising a U-shaped capture pocket configured to capture and retain the sample, the vitrification device further comprising a bypass channel on a side of the island and extending between the sample chamber and the input portion of the waste reservoir.

11. A method for preparing a sample, comprising:
delivering a sample into a sample chamber of a vitrification device and adjacent a filtering mechanism separating the sample chamber from a waste reservoir of the vitrification device, wherein the filtering mechanism is coupled to the sample chamber; and
treating the sample with a first fluid by receiving the first fluid via an input port, pushing the first fluid from the input port, through the sample chamber, across the filtering mechanism, and into the waste reservoir with a fluidic force, while the filtering mechanism retains the sample within the sample chamber;
wherein pushing the first fluid into the waste reservoir initiates capillary action in the filtering mechanism resulting in the capillary action drawing subsequent fluids through the sample chamber and into the waste reservoir;
wherein the filtering mechanism comprises a filtration grate positioned on an island between the sample chamber and an input portion of the waste reservoir, the island comprising a U-shaped capture pocket configured to capture and retain the sample, the vitrification device further comprising a bypass channel on a side of the island and extending between the sample chamber and the input portion of the waste reservoir.

12. The method of claim 11, further comprising treating the sample with a second fluid by drawing the second fluid through the sample chamber and into the waste reservoir via capillary action, while the filtering mechanism retains the sample within the sample chamber.

13. The method of claim 12, comprising holding, simultaneously by the waste reservoir, the first fluid and the second fluid within a handle of the vitrification device subsequent to the treating the sample with the first fluid and the treating the sample with the second fluid.

14. The method of claim 11, further comprising viewing the sample in the sample chamber through a viewing window in the sample chamber, the viewing window made of a different material than a remainder of the vitrification device.

15. The method of claim 11, further comprising vitrifying the sample in the sample chamber.

16. The method of claim 15, wherein the sample is vitrified by contacting the sample chamber with liquid nitrogen.

17. The method of claim 15, further comprising thawing the sample by contacting the sample chamber with a warm solution.

18. The method of claim 11, comprising holding, by the waste reservoir, the first fluid within a handle of the vitrification device subsequent to the treating the sample with the first fluid.

\* \* \* \* \*